(12) United States Patent
Willson et al.

(10) Patent No.: US 6,911,530 B1
(45) Date of Patent: Jun. 28, 2005

(54) HAEMOPOIETIN RECEPTOR AND GENETIC SEQUENCES ENCODING SAME

(75) Inventors: Tracy Willson, North Balwyn (AU); Nicos A. Nicola, Mont Albert (AU); Douglas J. Hilton, Warrandyte (AU); Donald Metcalf, Balwyn (AU); Jian Guo Zhang, Hoppers Crossing (AU)

(73) Assignee: Amrad Operations, Pty., Ltd., Richmond (AU)

( * ) Notice: Subject to any disclaimer, the term of this patent is extended or adjusted under 35 U.S.C. 154(b) by 390 days.

(21) Appl. No.: 09/688,286

(22) Filed: Oct. 13, 2000

Related U.S. Application Data

(62) Division of application No. 09/051,843, filed on Oct. 23, 1996.

(30) Foreign Application Priority Data

| Oct. 23, 1995 | (AU) | PN-6135 |
|---|---|---|
| Dec. 22, 1995 | (AU) | PN-7276 |
| Sep. 9, 1996 | (AU) | PO-2208 |

(51) Int. Cl.$^7$ .................. C07K 16/00; C07K 14/00; A61K 39/395; C07N 15/11

(52) U.S. Cl. .................. 530/387.1; 580/388.1; 580/388.15; 580/388.27; 580/387.9; 580/300; 580/350; 424/143.1; 435/7.1; 435/320.1; 435/69.1; 536/23.1

(58) Field of Search ............... 530/387.1, 387.9, 530/388.1, 388.15, 388.23; 424/300, 350, 143.1; 435/7.1, 320.1, 69.1; 536/23.1

(56) References Cited

U.S. PATENT DOCUMENTS

| 5,508,164 A | 4/1996 | Kausch et al. |
|---|---|---|
| 5,574,136 A | 11/1996 | Nagata et al. |

FOREIGN PATENT DOCUMENTS

| WO | WO96/11213 | 4/1996 |
|---|---|---|
| WO | WO97/20926 | 6/1997 |

OTHER PUBLICATIONS

Hilton, et al. (Jan. 1996) "Cloning and Characterization of a Binding Subunit of the Interleukin 13 Receptor that is also a Component of the Interleukin 4 Receptor", *Proc. Natl. Acad. Sci. USA* 93:497–501.

Lin, C.C., et al. "Differential Fluorescent Staining of Human Chromosomes with Daunomycin and Adriamycin—The D Bands," *Science*, vol. 190, p. 61–63, Oct. 3, 1975.

Matthews, et al. (Jan. 1, 1995) "Function of the Interleukin–2 (IL–2) Receptor γ–Chain in Biologic Responses, of X–Linked Severe Combined Immunodeficient B Cells to IL–2, IL–4, IL–13 and IL–15", *Blood* 85(1):38–42.

Miloux, et al. (1997) "Cloning of the Human IL–13Rα1 Chain and Reconstitution with the IL–4Rα of a Functional IL–4/IL–13 Receptor Complex", *FEBS Letters* 401:163–166.

Obiri, et al. (Apr. 14, 1995) "Receptor for Interleukin 18: Interaction with Interleukin 4 by a Mechanism that does not Involve the Common γ Chain Shared by Receptors for Interleukins 2, 4, 7, 9 and 15", *The Journal of Biological Chemistry* 270(16):8797–8804.

Obiri, et al. "The IL–13 Receptor Structure Differs on Various Cell Types and may Share More than One Component with IL–4 Receptor", *The Journal of Immunology*:756–764, Jan. 15, 1997.

Smerz–Bertling, et al. (Jan. 13, 1995) "Both Interleukin 4 and Interleukin 13 Induce Tyrosine Phosphorylation of the 140–kDa Subunit of the Interleukin 4 Receptor", *The Journal of Biological Chemistry* 270(2):966–970.

Vita, et al. (Feb. 24, 1995) "Characterization and Comparison of the Interleukin 13 Receptor with the Interleukin 4 Receptor on Several Cell Types", *The Journal of Biological Chemistry* 270(8):3512–3517.

Zhang, et al. (Apr. 4, 1997) "Indentification, Purification and Characterization of a Soluble Interleukin (IL)–13–Binding Protein", *The Journal of Biological Chemistry* 272(14):9474–9480.

Zurawski, et al. (1993) "Receptors for Interleukin–13 and Interleukin–4 are Complex and Share a Novel Component that Functions in Signal Transduction", *The EMBO Journal* 12(7):2663–2670.

Zurawski, et al. (Jun. 9, 1995) "The Primary Binding Subunit of the Human Interleukin–4 Receptor is also a Component of the Interleukin–13 Receptor", *The Journal of Biological Chemistry* 270(23):13869–13878.

D. Caput, et al. (1996) "Cloning and Characterization of a Specific Interleukin (IL)–13 Binding Protein Structurally Related to the IL–5 Receptor α Chain" *Journal of Biological Chemistry*, 271(28):16921–16926.

N.A. Nicola (1994) Guidebook to Cytokines and Their Receptors, Oxford University Press: New York, New York.

N. Vita, et al. (1995) "Characterization and Comparison of the Interleukin 13 Recpetor with the Interleukin 4 Receptor on Several Cell Types" The Journal of Biological Chemistry 270(8):3512–3517.

N. Harada, et al. (1990) "Expression Cloning of a cDNA Encoding the Murine Interleukin Receptor Based on Ligand Binding" Proc. Natl. Acad. Sci., USA 87:857–861.

*Primary Examiner*—Yvonne Eyler
*Assistant Examiner*—Nirmal S. Basi
(74) *Attorney, Agent, or Firm*—Scully, Scott, Murphy & Presser

(57) ABSTRACT

The present invention relates generally to a novel haemopoietin receptor or components or part thereof and to genetic sequences encoding same. The receptor molecules and their components and/or parts and the genetic sequences encoding same of the present invention are useful in the development of a wide range of agonists, antagonists, therapeutics and diagnostic reagents based on ligand interaction with its receptor.

15 Claims, 24 Drawing Sheets

```
-60    tgaaaagatagaataaatggcctcgtg

1    ATGGCGCGGCCAGCGCTGCTGGGCGAG
  1     M   A   R   P   A   L   L   G   E

61    GGCCAAGTTGCCGCGGCCACAGAAGTT
 21     G   Q   V   A   A   A   T   E   V

121    GAAAATCTCTGCACGATAATATGGACG
 41     E   N   L   C   T   I   I   W   T

181    ACTCTCAGATATTTTAGTCACTTTGAT
 61     T   L   R   Y   F   S   H   F   D

241    CATCGTAAAGAGGAATTACCCCTGGAT
 81     H   R   K   E   E   L   P   L   D

301    AGTGCCAATGAAAGTGAGAAGCCTAGC
101     S   A   N   E   S   E   K   P   S

361    GGTGATCCTGAGTCCGCTGTGACTGAG
121     G   D   P   E   S   A   V   T   E

421    AAGTGTTCCTGGCTCCCTGGAAGGAAT
141     K   C   S   W   L   P   G   R   N
```

Fig.1A

```
ccgaattcggcacgagccgaggcgagggcctgc

CTGTTGGTGCTGCTACTGTGGACCGCCACCGTG
 L   L   V   L   L   L   W   T   A   T   V

CAGCCACCTGTGACGAATTTGAGCGTCTCTGTC
 Q   P   P   V   T   N   L   S   V   S   V

TGGAGTCCTCCTGAAGGAGCCAGTCCAAATTGC
 W   S   P   P   E   G   A   S   P   N   C

GACCAACAGGATAAGAAAATTGCTCCAGAAACT
 D   Q   Q   D   K   K   I   A   P   E   T

GAGAAAATCTGTCTGCAGGTGGGCTCTCAGTGT
 E   K   I   C   L   Q   V   G   S   Q   C

CCTTTGGTGAAAAAGTGCATCTCACCCCCTGAA
 P   L   V   K   K   C   I   S   P   P   E

CTCAAGTGCATTTGGCATAACCTGAGCTATATG
 L   K   C   I   W   H   N   L   S   Y   M

ACAAGCCCTGACACACTATACTCTGTACTAT
 T   S   P   D   T   H   Y   T   L   Y   Y
```

Fig. 1B

| | |
|---|---|
| 481 | TGGTACAGCAGCCTGGACAAAAGTCGT |
| 161 | W Y S S L E K S R |
| 541 | ATTGCTTGTTCCTTTAAATTGACTAAA |
| 181 | I A C S F K L T K |
| 601 | ATAATGGTCAAGGATAATGCTGGGAAA |
| 201 | I M V K D N A G K |
| 661 | TCCTATGTGAAACCTGATCCTCCACAT |
| 221 | S Y V K P D P P H |
| 721 | TTAGTGCAGTGGAAGAATCCACAAAAT |
| 241 | L V Q W K N P Q N |
| 781 | GTCAATAATACTCAAACCGACCGACAT |
| 261 | V N N T Q T D R H |
| 841 | AATTCCGAATCTGATAGAAACATGGAG |
| 281 | N S E S D R N M E |
| 901 | GCCGACGCTGTCTACACAGTCAGAGTA |
| 301 | A D A V Y T V R V |
| 961 | AACAAACTGTGGAGTGATTGGAGTGAA |
| 321 | N K L W S D W S E |

*Fig. 1C*

```
CAATGTGAAAACATCTATAGAGAAGGTCAACAC
 Q  C  E  N  I  Y  R  E  G  Q  H

GTGGAACCTAGTTTTGAACATCAGAACGTTCAA
 V  E  P  S  F  E  H  Q  N  V  Q

ATTAGGCCATCCTGCAAAATAGTGTCTTTAACT
 I  R  P  S  C  K  I  V  S  L  T

ATTAAACATCTTCTCCTCAAAAATGGTGCCTTA
 I  K  H  L  L  L  K  N  G  A  L

TTTAGAAGCAGATGCTTAACTTATGAAGTGGAG
 F  R  S  R  C  L  T  Y  E  V  E

AATATTTTAGAGGTTGAAGAGGACAAATGCCAG
 N  I  L  E  V  E  E  D  K  C  Q

GGTACAAGTTGTTTCCAACTCCCTGGTGTTCTT
 G  T  S  C  F  Q  L  P  G  V  L

AGAGTCAAAACAAACAAGTTATGCTTTGATGAC
 R  V  K  T  N  K  L  C  F  D  D

GCACAGAGTATAGGTAAGGAGCAAAACTCCACC
 A  Q  S  I  G  K  E  Q  N  S  T
```

*Fig. 1D*

```
1021    TTCTACACCACCATGTTACTCACCATT
 341     F  Y  T  T  M  L  L  T  I

1081    CTTTTTTACCTGAAAAGGCTTAAGATC
 361     L  F  Y  L  K  R  L  K  I

1141    ATTTTTAAAGAAATGTTTGGAGACCAG
 381     I  F  K  E  M  F  G  D  Q

1201    ATCTATGAGAACAATCCAAAGAAGAA
 401     I  Y  E  K  Q  S  K  E  E

1261    AAAGCAGCTCCTTGAtggggagaagtg
 421     K  A  A  P  *

1321    gatttattgcattctccatttgttatc
1381    cttgaaaacaggcagctcctaagagc
1441    ccaaacccaaggagctccttccaaga
1501    ccctaaaagcagatgttttgccaaatc
1561    accatcaattcatctaatcaggaattg
```

*Fig. IE*

```
CCAGTCTTTGTCGCAGTGGCAGTCATAATCCTC
 P   V  F  V  A  V  A  V  I  I  L

ATTATATTTCCTCCAATTCCTGATCCTGGCAAG
 I  I  F  P  P  I  P  D  P  G  K

AATGATGATACCCTGCACTGGAAGAAGTATGAC
 N  D  D  T  L  H  W  K  K  Y  D

ACGGATTCTGTAGTGCTGATAGAAAACCTGAAG
 T  D  S  V  V  L  I  E  N  L  K atttctttcttgccttcaatgtgaccctgtaa tggggacttgttaaatagaaactgaaactact
cacaggtcttgatgtgactttgcattgaaaac
aaagcaagagttcttctcgttccttgttccaat
cccaaactagaggacaaagacaaggggacaatg
tgatggcttcctaaggaatctgcttgctctg
```

*Fig. IF*

(major)

DYKDD DDYKD DDESR TEVQP PVTXL SV
1     5     10    15    20    25

(minor)

ASISS SDYKD DDESR TEVQP PVTXL SV
1     5     10    15    20    25

| 14/24 | 15/24 |
|---|---|
| 16/24 | 17/24 |
| 18/24 | 19/24 |
| 20/24 | 21/24 |
| 22/24 | 23/24 |

Fig. 7

| | | |
|---|---|---|
| H | | gagtctaacacggaccaaggagtttaac |
| M | -60 | tgaaaagatagaataaatggcctcgtgc |
| H | | M E W P A R L C G |
| H | | ATGGAGTGGCCGGCGCGGCTCTGCGGGC |
| | | \*    \* \*    \* |
| M | 1 | ATGGCGCGGCCAGCGCTGCTGGGCGAGC |
| M | 1 | M A R P A L L G E |
| H | | G G G G A P T E T |
| H | | GGGGGCGGGGGCGCGCCTACGGAAACTC |
| | | \*         \* \* \* |
| M | 61 | GGCCAAGTTGCCGCGGCCACAGAAGTTC |
| M | 21 | G Q V A A A T E V |
| H | | E N L C T V I W T |
| H | | GAAAACCTCTGCACAGTAATATGGACAT |
| | | \* \* \* \* \*    \* \* \* |
| M | 121 | GAAAATCTCTGCACGATAATATGGACGT |
| M | 41 | E N L C T I I W T |
| H | | S L W Y F S H F G |
| H | | AGTCTATGGTATTTTAGTCATTTTGGCG |
| | | \*    \* \* \* \* \* |
| M | 181 | ACTCTCAGATATTTTAGTCACTTTGATG |
| M | 61 | T L R Y F S H F D |

Fig. 7A

```
acgtgcggccgggttccgaggcgagaggctgc
 . . . .        . . . . . . . . . . . .   .   . . . .
cgaattcggcacgagccgaggcgagggcctgc
```

```
 L   W   A   L   L   L   C   A   G   G   G
TGTGGGCGCTGCTGCTCTGCGCCGGCGGCGGGGGC
 *           *   *   *
TGTTGGTGCTGCTACTGTGGACCGCCACCGTG- - -
 L   L   V   L   L   L   W   T   A   T   V   -
```

```
 Q   P   P   V   T   N   L   S   V   S   V
AGCCACCTGTGACAATTTGAGTGTCTCTGTT
 *   *   *   *   *   *   *   *   *   *   *
AGCCACCTGTGACGAATTTGAGCGTCTCTGTC
 Q   P   P   V   T   N   L   S   V   S   V
```

```
 W   N   P   P   E   G   A   S   S   N   C
GGAATCCACCCGAGGGAGCCAGCTCAAATTGT
 *   *   *   *   *   *   *       *   *
GGAGTCCTCCTGAAGGAGCCAGTCCAAATTGC
 W   S   P   P   E   G   A   S   P   N   C
```

```
 D   K   Q   D   K   K   I   A   P   E   T
ACAAACAAGATAAGAAAATAGCTCCGGAAACT
 *   *   *   *   *   *   *   *   *   *
ACCAACAGGATAAGAAAATTGCTCCAGAAACT
 D   Q   Q   D   K   K   I   A   P   E   T
```

Fig. 7B

```
H           R  R  S  I  E  V  P  L  N
H           CGTCGTTCAATAGAAGTACCCCTGAATG
            *         *       *  *
M    241    CATCGTAAAGAGGAATTACCCCTGGATG
M    81     H  R  K  E  E  L  P  L  D

H           S  T  N  E  S  E  K  P  S
H           AGCACCAATGAGAGTGAGAAGCCTAGCA
            *     *  *  *  *  *  *  *
M    301    AGTGCCAATGAAAGTGAGAAGCCTAGCC
M    101    S  A  N  E  S  E  K  P  S

H           G  D  P  E  S  A  V  T  E
H           GGTGATCCTGAGTCTGCTGTGACTGAAC
            *  *  *  *  *  *  *  *  *
M    361    GGTGATCCTGAGTCCGCTGTGACTGAGC
M    121    G  D  P  E  S  A  V  T  E

H           K  C  S  W  L  P  G  R  N
H           AAGTGTTCTTGGCTCCCTGGAAGGAATA
            *  *  *  *  *  *  *  *  *
M    421    AAGTGTTCCTGGCTCCCTGGAAGGAATA
M    141    K  C  S  W  L  P  G  R  N

H           W  H  R  S  L  E  K  I  H
H           TGGCACAGAAGCCTGGAAAAAATTCATC
```

Fig. 7C

```
E   R   I   C   L   Q   V   G   S   Q   C
AGAGGATTTGTCTGCAAGTGGGGTCCCAGTGT
 *   *   *   *   *   *   *   *   *   *
AGAAAATCTGTCTGCAGGTGGGCTCTCAGTGT
E   K   I   C   L   Q   V   G   S   Q   C

I   L   V   E   K   C   I   S   P   P   E
TTTTGGTTGAAAAATGCATCTCACCCCAGAA
 *   *   *   *   *   *   *   *   *   *
CTTTGGTGAAAAAGTGCATCTCACCCCTGAA
P   L   V   K   K   C   I   S   P   P   E

L   Q   C   I   W   H   N   L   S   Y   M
TTCAATGCATTTGGCACAACCTGAGCTACATG
 *   *   *   *   *   *   *   *   *   *
TCAAGTGCATTTGGCATAACCTGAGCTATATG
L   K   C   I   W   H   N   L   S   Y   M

T   S   P   D   T   N   Y   T   L   Y   Y
CCAGTCCCGACACTAACTATACTCTCTACTAT
 *   *   *   *   *       *   *   *   *   *
CAAGCCCTGACACACACTATACTCTGTACTAT
T   S   P   D   T   H   Y   T   L   Y   Y

Q   C   E   N   I   F   R   E   G   Q   Y
AATGTGAAAACATCTTTAGAGAAGGCCAATAC
```

Fig. 7D

```
                  *             *   *   *   *
M  481   TGGTACAGCAGCCTGGAGAAAAGTCGTC
M  161    W   Y   S   S   L   E   K   S   R

H         F   G   C   S   F   D   L   T   K
H        TTTGGTTGTTCCTTTGATCTGACCAAAG
              *   *   *       *   *   *
M  541   ATTGCTTGTTCCTTTAAATTGACTAAAG
M  181    I   A   C   S   F   K   L   T   K

H         Q   I   M   V   K   D   N   A   G
H        CAAATAATGGTCAAGGATAATGCAGGAA
          *   *   *   *   *   *   *   *   *
M  601   CAAATAATGGTCAAGGATAATGCTGGGA
M  201    Q   I   M   V   K   D   N   A   G

H         T   S   R   V   K   P   D   P   P
H        ACTTCCCGTGTGAAACCTGATCCTCCAC
          *   *       *   *   *   *   *   *
M  661   ACTTCCTATGTGAAACCTGATCCTCCAC
M  221    T   S   Y   V   K   P   D   P   P

H         L   Y   V   Q   W   E   N   P   Q
H        CTATATGTGCAATGGGAGAATCCACAGA
          *       *   *   *       *   *   *
M  721   TTATTAGTGCAGTGGAAGAATCCACAAA
M  241    L   L   V   Q   W   K   N   P   Q
```

Fig.7E

```
  *   *   *   *   *       *   *   *   *
AATGTGAAAACATCTATAGAGAAGGTCAACAC
Q   C   E   N   I   Y   R   E   G   Q   H

V   K   D   S   S   F   E   Q   H   S   V
TGAAGGATTCCAGTTTTGAACAACACAGTGTC
*           *   *   *               *
TGGAACCT---AGTTTTGAACATCAGAACG TT
V   E   P   -   S   F   E   H   Q   N   V

K   I   K   P   S   F   N   I   V   P   L
AAATTAAACCATCCTTCAATATAGTGCCTTTA
*   *       *   *           *   *       *
AAATTAGGCCATCCTGCAAAATAGTGTCTTTA
K   I   R   P   S   C   K   I   V   S   L

H   I   K   N   L   S   F   H   N   D   D
ATATTAAAACCTCTCCTTCCACAATGATGAC
*   *   *       *               *
ATATTAAACATCTTCTCCTCAAAAATGGTGCC
H   I   K   H   L   L   K   N   G   A

N   F   I   S   R   C   L   F   Y   E   V
ATTTTATTAGCAGATGCCTATTTTATGAAGTA
*   *       *   *   *   *           *   *   *
ATTTTAGAAGCAGATGCTTAACTTATGAAGTG
N   F   R   S   R   C   L   T   Y   E   V
```

*Fig. 7F*

```
H            E   V   N   N   S   Q   T   E   T
H            GAAGTCAATAACAGCCAAACTGAGACAC
             *   *   *   *       *   *
M   781      GAGGTCAATAATACTCAAACCGACCGAC
M   261      E   V   N   N   T   Q   T   D   R

H            E   N   P   E   F   E   R   N   V
H            GAGAATCCAGAATTTGAGAGAAATGTGG
                 *       *           *   *
M   841      CAGAATTCCGAATCTGATAGAAACATGG
M   281      Q   N   S   E   S   D   R   N   M

H            L   P   D   T   L   N   T   V   R
H            CTTCCTGATACTTTGAACACAGTCAGAA
             *       *           *   *   *
M   901      CTTGCCGACGCTGTCTACACAGTCAGAG
M   301      L   A   D   A   V   Y   T   V   R

H            D   D   K   L   W   S   N   W   S
H            GATGACAAACTCTGGAGTAATTGGAGCC
                 *   *   *   *   *       *   *
M   961      GACAACAAACTGTGGAGTGATTGGAGTG
M   321      D   N   K   L   W   S   D   W   S

H            T   L   Y   I   T   M   L   L   I
H            ACACTCTACATAACCATGTTACTCATTG
```

Fig. 7G

```
H   N   V   F   Y   V   Q   E   A   K   C
ATAATGTTTTCTACGTCCAAGAGGCTAAATGT
 *   *       *       *       *   *
ATAATATTTTAGAGGTTGAAGAGGACAAATGC
H   N   I   L   E   V   E   E   D   K   C

E   N   T   S   C   F   M   V   P   G   V
AGAATACATCTTGTTTCATGGTCCCTGGTGTT
 *   *   *   *   *           *   *   *
AGGGTACAAGTTGTTTCCAACTCCCTGGTGTT
E   G   T   S   C   F   Q   L   P   G   V

I   R   V   K   T   N   K   L   C   Y   E
TAAGAGTCAAAACAAATAAGTTATGCTATGAG
 *   *   *   *   *   *   *   *
TAAGAGTCAAAACAAACAAGTTATGCTTTGAT
V   R   V   K   T   N   K   L   C   F   D

Q   E   M   S   I   G   K   K   R   N   S
AAGAAATGAGTATAGGTAAGAAGCGCAATTCC
 *   *   *   *           *   *
AAGCACAGAGTATAGGTAAGGAGCAAAACTCC
E   A   Q   S   I   G   K   E   Q   N   S

V   P   V   I   V   A   G   A   I   I   V
TTCCAGTCATCGTCGCAGGTGCAATCATAGTA
```

*Fig. 7H*

```
              *        *       *  *   *   *
M  1021  ACCTTCTACACCACCATGTTACTCACCA
M   341    T  F  Y  T  T  M  L  L  T

H           L  L  L  Y  L  K  R  L  K
H         CTCCTGCTTTACCTAAAAGGCTCAAGA
           *  *    *  *  *  *  *  *
M  1081  CTCCTTTTTTACCTGAAAAGGCTTAAGA
M   361    L  L  F  Y  L  K  R  L  K

H           K  I  F  K  E  M  F  G  D
H         AAGATTTTTAAAGAAATGTTTGGAGACC
           *  *  *  *  *  *  *  *  *
M  1141  AAGATTTTTAAAGAAATGTTTGGAGACC
M   381    K  I  F  K  E  M  F  G  D

H           D  I  Y  E  K  Q  T  K  E
H         GACATCTATGAGAAGCAAACCAAGGAGG
           *  *  *  *  *  *     *  *
M  1201  GACATCTATGAGAAACAATCCAAAGAAG
M   401    D  I  Y  E  K  Q  S  K  E

H           K  K  A  S  Q  *
H         AAGAAAGCCTCTCAGTGAtggagataat
           *  *  *
M  1261  AAGAAAGCAGCTCCTTGAtggggagaag
M   421    K  K  A  A  P  *
```

Fig. 71

```
         *    *        *    *           *         *
        TTCCAGTCTTTGTCGCAGTGGCAGTCATAATC
         I   P   V   F   V   A   V   A   V   I   I

I   I   I   F   P   P   I   P   D   P   G
        TTATTATATTCCTCCAATTCCTGATCCTGGC
        *   *   *   *   *   *   *   *   *   *   *
        TCATTATATTTCCTCCAATTCCTGATCCTGGC
         I   I   I   F   P   P   I   P   D   P   G

Q   N   D   D   T   L   H   W   K   K   Y
        AGAATGATGATACTCTGCACTGGAAGAAGTAC
        *   *   *   *   *   *   *   *   *   *   *
        AGAATGATGATACCCTGCACTGGAAGAAGTAT
         Q   N   D   D   T   L   H   W   K   K   Y

E   T   D   S   V   V   L   I   E   N   L
        AAACCGACTCTGTAGTGCTGATAGAAAACCTG
        *   *   *   *   *   *   *   *   *   *   *
        AAACGGATTCTGTAGTGCTGATAGAAAACCTG
         E   T   D   S   V   V   L   I   E   N   L ttattttaccttcactgtgaccttgagaaga tgatttctttcttgccttcaatgtgaccctgt
```

Fig. 7J

SEQUENCE LISTING

<160> NUMBER OF SEQ ID NOS: 12

<210> SEQ ID NO 1
<211> LENGTH: 1680
<212> TYPE: DNA
<213> ORGANISM: Mus musculus
<220> FEATURE:
<221> NAME/KEY: CDS
<222> LOCATION: (61)..(1332)
<223> OTHER INFORMATION:

<400> SEQUENCE: 1

| | | |
|---|---|---|
| tgaaaagata gaataaatgg cctcgtgccg aattcggcac gagccgaggc gagggcctgc | 60 |

| | | | | | | | | | | | | | | | | |
|---|---|---|---|---|---|---|---|---|---|---|---|---|---|---|---|---|
| atg | gcg | cgg | cca | gcg | ctg | ctg | ggc | gag | ctg | ttg | gtg | ctg | cta | ctg | tgg | 108 |
| Met | Ala | Arg | Pro | Ala | Leu | Leu | Gly | Glu | Leu | Leu | Val | Leu | Leu | Leu | Trp | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| acc | gcc | acc | gtg | ggc | caa | gtt | gcc | gcg | gcc | aca | gaa | gtt | cag | cca | cct | 156 |
| Thr | Ala | Thr | Val | Gly | Gln | Val | Ala | Ala | Ala | Thr | Glu | Val | Gln | Pro | Pro | |
| | | | 20 | | | | | 25 | | | | | 30 | | | |

| | | | | | | | | | | | | | | | | |
|---|---|---|---|---|---|---|---|---|---|---|---|---|---|---|---|---|
| gtg | acg | aat | ttg | agc | gtc | tct | gtc | gaa | aat | ctc | tgc | acg | ata | ata | tgg | 204 |
| Val | Thr | Asn | Leu | Ser | Val | Ser | Val | Glu | Asn | Leu | Cys | Thr | Ile | Ile | Trp | |
| | | 35 | | | | | 40 | | | | | 45 | | | | |

| | | | | | | | | | | | | | | | | |
|---|---|---|---|---|---|---|---|---|---|---|---|---|---|---|---|---|
| acg | tgg | agt | cct | cct | gaa | gga | gcc | agt | cca | aat | tgc | act | ctc | aga | tat | 252 |
| Thr | Trp | Ser | Pro | Pro | Glu | Gly | Ala | Ser | Pro | Asn | Cys | Thr | Leu | Arg | Tyr | |
| | 50 | | | | | 55 | | | | | 60 | | | | | |

| | | | | | | | | | | | | | | | | |
|---|---|---|---|---|---|---|---|---|---|---|---|---|---|---|---|---|
| ttt | agt | cac | ttt | gat | gac | caa | cag | gat | aag | aaa | att | gct | cca | gaa | act | 300 |
| Phe | Ser | His | Phe | Asp | Asp | Gln | Gln | Asp | Lys | Lys | Ile | Ala | Pro | Glu | Thr | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| cat | cgt | aaa | gag | gaa | tta | ccc | ctg | gat | gag | aaa | atc | tgt | ctg | cag | gtg | 348 |
| His | Arg | Lys | Glu | Glu | Leu | Pro | Leu | Asp | Glu | Lys | Ile | Cys | Leu | Gln | Val | |
| | | | | 85 | | | | | 90 | | | | | 95 | | |

| | | | | | | | | | | | | | | | | |
|---|---|---|---|---|---|---|---|---|---|---|---|---|---|---|---|---|
| ggc | tct | cag | tgt | agt | gcc | aat | gaa | agt | gag | aag | cct | agc | cct | ttg | gtg | 396 |
| Gly | Ser | Gln | Cys | Ser | Ala | Asn | Glu | Ser | Glu | Lys | Pro | Ser | Pro | Leu | Val | |
| | | | 100 | | | | | 105 | | | | | 110 | | | |

| | | | | | | | | | | | | | | | | |
|---|---|---|---|---|---|---|---|---|---|---|---|---|---|---|---|---|
| aaa | aag | tgc | atc | tca | ccc | cct | gaa | ggt | gat | cct | gag | tcc | gct | gtg | act | 444 |
| Lys | Lys | Cys | Ile | Ser | Pro | Pro | Glu | Gly | Asp | Pro | Glu | Ser | Ala | Val | Thr | |
| | | 115 | | | | | 120 | | | | | 125 | | | | |

| | | | | | | | | | | | | | | | | |
|---|---|---|---|---|---|---|---|---|---|---|---|---|---|---|---|---|
| gag | ctc | aag | tgc | att | tgg | cat | aac | ctg | agc | tat | atg | aag | tgt | tcc | tgg | 492 |
| Glu | Leu | Lys | Cys | Ile | Trp | His | Asn | Leu | Ser | Tyr | Met | Lys | Cys | Ser | Trp | |
| | 130 | | | | | 135 | | | | | 140 | | | | | |

| | | | | | | | | | | | | | | | | |
|---|---|---|---|---|---|---|---|---|---|---|---|---|---|---|---|---|
| ctc | cct | gga | agg | aat | aca | agc | cct | gac | aca | cac | tat | act | ctg | tac | tat | 540 |
| Leu | Pro | Gly | Arg | Asn | Thr | Ser | Pro | Asp | Thr | His | Tyr | Thr | Leu | Tyr | Tyr | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| tgg | tac | agc | agc | ctg | gag | aaa | agt | cgt | caa | tgt | gaa | aac | atc | tat | aga | 588 |
| Trp | Tyr | Ser | Ser | Leu | Glu | Lys | Ser | Arg | Gln | Cys | Glu | Asn | Ile | Tyr | Arg | |
| | | | | 165 | | | | | 170 | | | | | 175 | | |

| | | | | | | | | | | | | | | | | |
|---|---|---|---|---|---|---|---|---|---|---|---|---|---|---|---|---|
| gaa | ggt | caa | cac | att | gct | tgt | tcc | ttt | aaa | ttg | act | aaa | gtg | gaa | cct | 636 |
| Glu | Gly | Gln | His | Ile | Ala | Cys | Ser | Phe | Lys | Leu | Thr | Lys | Val | Glu | Pro | |
| | | | 180 | | | | | 185 | | | | | 190 | | | |

| | | | | | | | | | | | | | | | | |
|---|---|---|---|---|---|---|---|---|---|---|---|---|---|---|---|---|
| agt | ttt | gaa | cat | cag | aac | gtt | caa | ata | atg | gtc | aag | gat | aat | gct | ggg | 684 |
| Ser | Phe | Glu | His | Gln | Asn | Val | Gln | Ile | Met | Val | Lys | Asp | Asn | Ala | Gly | |
| | | 195 | | | | | 200 | | | | | 205 | | | | |

| | | | | | | | | | | | | | | | | |
|---|---|---|---|---|---|---|---|---|---|---|---|---|---|---|---|---|
| aaa | att | agg | cca | tcc | tgc | aaa | ata | gtg | tct | tta | act | tcc | tat | gtg | aaa | 732 |
| Lys | Ile | Arg | Pro | Ser | Cys | Lys | Ile | Val | Ser | Leu | Thr | Ser | Tyr | Val | Lys | |
| | 210 | | | | | 215 | | | | | 220 | | | | | |

| | | | | | | | | | | | | | | | | |
|---|---|---|---|---|---|---|---|---|---|---|---|---|---|---|---|---|
| cct | gat | cct | cca | cat | att | aaa | cat | ctt | ctc | ctc | aaa | aat | ggt | gcc | tta | 780 |
| Pro | Asp | Pro | Pro | His | Ile | Lys | His | Leu | Leu | Leu | Lys | Asn | Gly | Ala | Leu | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| tta | gtg | cag | tgg | aag | aat | cca | caa | aat | ttt | aga | agc | aga | tgc | tta | act | 828 |

-continued

| | | |
|---|---|---|
| Leu Val Gln Trp Lys Asn Pro Gln Asn Phe Arg Ser Arg Cys Leu Thr<br>245 250 255 | | |
| tat gaa gtg gag gtc aat aat act caa acc gac cga cat aat att tta<br>Tyr Glu Val Glu Val Asn Asn Thr Gln Thr Asp Arg His Asn Ile Leu<br>260 265 270 | | 876 |
| gag gtt gaa gag gac aaa tgc cag aat tcc gaa tct gat aga aac atg<br>Glu Val Glu Glu Asp Lys Cys Gln Asn Ser Glu Ser Asp Arg Asn Met<br>275 280 285 | | 924 |
| gag ggt aca agt tgt ttc caa ctc cct ggt gtt ctt gcc gac gct gtc<br>Glu Gly Thr Ser Cys Phe Gln Leu Pro Gly Val Leu Ala Asp Ala Val<br>290 295 300 | | 972 |
| tac aca gtc aga gta aga gtc aaa aca aac aag tta tgc ttt gat gac<br>Tyr Thr Val Arg Val Arg Val Lys Thr Asn Lys Leu Cys Phe Asp Asp<br>305 310 315 320 | | 1020 |
| aac aaa ctg tgg agt gat tgg agt gaa gca cag agt ata ggt aag gag<br>Asn Lys Leu Trp Ser Asp Trp Ser Glu Ala Gln Ser Ile Gly Lys Glu<br>325 330 335 | | 1068 |
| caa aac tcc acc ttc tac acc acc atg tta ctc acc att cca gtc ttt<br>Gln Asn Ser Thr Phe Tyr Thr Thr Met Leu Leu Thr Ile Pro Val Phe<br>340 345 350 | | 1116 |
| gtc gca gtg gca gtc ata atc ctc ctt ttt tac ctg aaa agg ctt aag<br>Val Ala Val Ala Val Ile Ile Leu Leu Phe Tyr Leu Lys Arg Leu Lys<br>355 360 365 | | 1164 |
| atc att ata ttt cct cca att cct gat cct ggc aag att ttt aaa gaa<br>Ile Ile Ile Phe Pro Pro Ile Pro Asp Pro Gly Lys Ile Phe Lys Glu<br>370 375 380 | | 1212 |
| atg ttt gga gac cag aat gat gat acc ctg cac tgg aag aag tat gac<br>Met Phe Gly Asp Gln Asn Asp Asp Thr Leu His Trp Lys Lys Tyr Asp<br>385 390 395 400 | | 1260 |
| atc tat gag aaa caa tcc aaa gaa gaa acg gat tct gta gtg ctg ata<br>Ile Tyr Glu Lys Gln Ser Lys Glu Glu Thr Asp Ser Val Val Leu Ile<br>405 410 415 | | 1308 |
| gaa aac ctg aag aaa gca gct cct tgatggggag aagtgatttc tttcttgcct<br>Glu Asn Leu Lys Lys Ala Ala Pro<br>420 | | 1362 |
| tcaatgtgac cctgtgaaga tttattgcat tctccatttg ttatctgggg gacttgttaa | | 1422 |
| atagaaactg aaactactct tgaaaaacag gcagctccta agagccacag gtcttgatgt | | 1482 |
| gactttttgca ttgaaaaccc aaacccaaag gagctccttc caagaaaagc aagagttctt | | 1542 |
| ctcgttcctt gttccaatcc ctaaaagcag atgttttgcc aaatcccccaa actagaggac | | 1602 |
| aaagacaagg ggacaatgac catcaattca tctaatcagg aattgtgatg gcttcctaag | | 1662 |
| gaatctctgc ttgctctg | | 1680 |

<210> SEQ ID NO 2
<211> LENGTH: 424
<212> TYPE: PRT
<213> ORGANISM: Mus musculus

<400> SEQUENCE: 2

Met Ala Arg Pro Ala Leu Leu Gly Glu Leu Leu Val Leu Leu Leu Trp
1               5                   10                  15

Thr Ala Thr Val Gly Gln Val Ala Ala Ala Thr Glu Val Gln Pro Pro
            20                  25                  30

Val Thr Asn Leu Ser Val Ser Val Glu Asn Leu Cys Thr Ile Ile Trp
        35                  40                  45

Thr Trp Ser Pro Pro Glu Gly Ala Ser Pro Asn Cys Thr Leu Arg Tyr
    50                  55                  60

```
Phe Ser His Phe Asp Asp Gln Gln Asp Lys Lys Ile Ala Pro Glu Thr
 65                  70                  75                  80

His Arg Lys Glu Glu Leu Pro Leu Asp Glu Lys Ile Cys Leu Gln Val
                 85                  90                  95

Gly Ser Gln Cys Ser Ala Asn Glu Ser Glu Lys Pro Ser Pro Leu Val
            100                 105                 110

Lys Lys Cys Ile Ser Pro Pro Glu Gly Asp Pro Glu Ser Ala Val Thr
        115                 120                 125

Glu Leu Lys Cys Ile Trp His Asn Leu Ser Tyr Met Lys Cys Ser Trp
130                 135                 140

Leu Pro Gly Arg Asn Thr Ser Pro Asp Thr His Tyr Thr Leu Tyr Tyr
145                 150                 155                 160

Trp Tyr Ser Ser Leu Glu Lys Ser Arg Gln Cys Glu Asn Ile Tyr Arg
                165                 170                 175

Glu Gly Gln His Ile Ala Cys Ser Phe Lys Leu Thr Lys Val Glu Pro
            180                 185                 190

Ser Phe Glu His Gln Asn Val Gln Ile Met Val Lys Asp Asn Ala Gly
        195                 200                 205

Lys Ile Arg Pro Ser Cys Lys Ile Val Ser Leu Thr Ser Tyr Val Lys
    210                 215                 220

Pro Asp Pro Pro His Ile Lys His Leu Leu Leu Lys Asn Gly Ala Leu
225                 230                 235                 240

Leu Val Gln Trp Lys Asn Pro Gln Asn Phe Arg Ser Arg Cys Leu Thr
                245                 250                 255

Tyr Glu Val Glu Val Asn Asn Thr Gln Thr Asp Arg His Asn Ile Leu
            260                 265                 270

Glu Val Glu Glu Asp Lys Cys Gln Asn Ser Glu Ser Asp Arg Asn Met
        275                 280                 285

Glu Gly Thr Ser Cys Phe Gln Leu Pro Gly Val Leu Ala Asp Ala Val
290                 295                 300

Tyr Thr Val Arg Val Arg Val Lys Thr Asn Lys Leu Cys Phe Asp Asp
305                 310                 315                 320

Asn Lys Leu Trp Ser Asp Trp Ser Glu Ala Gln Ser Ile Gly Lys Glu
                325                 330                 335

Gln Asn Ser Thr Phe Tyr Thr Thr Met Leu Leu Thr Ile Pro Val Phe
            340                 345                 350

Val Ala Val Ala Val Ile Ile Leu Leu Phe Tyr Leu Lys Arg Leu Lys
        355                 360                 365

Ile Ile Ile Phe Pro Pro Ile Pro Asp Pro Gly Lys Ile Phe Lys Glu
370                 375                 380

Met Phe Gly Asp Gln Asn Asp Asp Thr Leu His Trp Lys Lys Tyr Asp
385                 390                 395                 400

Ile Tyr Glu Lys Gln Ser Lys Glu Glu Thr Asp Ser Val Val Leu Ile
                405                 410                 415

Glu Asn Leu Lys Lys Ala Ala Pro
                420

<210> SEQ ID NO 3
<211> LENGTH: 1383
<212> TYPE: DNA
<213> ORGANISM: human
<220> FEATURE:
<221> NAME/KEY: CDS
<222> LOCATION: (61)..(1338)
<223> OTHER INFORMATION:
```

-continued

<400> SEQUENCE: 3

```
gagtctaaca cggaccaagg agtttaacac gtgcggccgg gttccgaggc gagaggctgc    60 atg gag tgg ccg gcg cgg ctc tgc ggg ctg tgg gcg ctg ctg ctc tgc    108
Met Glu Trp Pro Ala Arg Leu Cys Gly Leu Trp Ala Leu Leu Leu Cys
1               5                   10                  15 gcc ggc ggc ggg ggc ggg ggc ggg ggc gcg cct acg gaa act cag cca    156
Ala Gly Gly Gly Gly Gly Gly Gly Gly Ala Pro Thr Glu Thr Gln Pro
            20                  25                  30 cct gtg aca aat ttg agt gtc tct gtt gaa aac ctc tgc aca gta ata    204
Pro Val Thr Asn Leu Ser Val Ser Val Glu Asn Leu Cys Thr Val Ile
        35                  40                  45 tgg aca tgg aat cca ccc gag gga gcc agc tca aat tgt agt cta tgg    252
Trp Thr Trp Asn Pro Pro Glu Gly Ala Ser Ser Asn Cys Ser Leu Trp
    50                  55                  60 tat ttt agt cat ttt ggc gac aaa caa gat aag aaa ata gct ccg gaa    300
Tyr Phe Ser His Phe Gly Asp Lys Gln Asp Lys Lys Ile Ala Pro Glu
65                  70                  75                  80 act cgt cgt tca ata gaa gta ccc ctg aat gag agg att tgt ctg caa    348
Thr Arg Arg Ser Ile Glu Val Pro Leu Asn Glu Arg Ile Cys Leu Gln
                85                  90                  95 gtg ggg tcc cag tgt agc acc aat gag agt gag aag cct agc att ttg    396
Val Gly Ser Gln Cys Ser Thr Asn Glu Ser Glu Lys Pro Ser Ile Leu
            100                 105                 110 gtt gaa aaa tgc atc tca ccc cca gaa ggt gat cct gag tct gct gtg    444
Val Glu Lys Cys Ile Ser Pro Pro Glu Gly Asp Pro Glu Ser Ala Val
        115                 120                 125 act gaa ctt caa tgc att tgg cac aac ctg agc tac atg aag tgt tct    492
Thr Glu Leu Gln Cys Ile Trp His Asn Leu Ser Tyr Met Lys Cys Ser
    130                 135                 140 tgg ctc cct gga agg aat acc agt ccc gac act aac tat act ctc tac    540
Trp Leu Pro Gly Arg Asn Thr Ser Pro Asp Thr Asn Tyr Thr Leu Tyr
145                 150                 155                 160 tat tgg cac aga agc ctg gaa aaa att cat caa tgt gaa aac atc ttt    588
Tyr Trp His Arg Ser Leu Glu Lys Ile His Gln Cys Glu Asn Ile Phe
                165                 170                 175 aga gaa ggc caa tac ttt ggt tgt tcc ttt gat ctg acc aaa gtg aag    636
Arg Glu Gly Gln Tyr Phe Gly Cys Ser Phe Asp Leu Thr Lys Val Lys
            180                 185                 190 gat tcc agt ttt gaa caa cac agt gtc caa ata atg gtc aag gat aat    684
Asp Ser Ser Phe Glu Gln His Ser Val Gln Ile Met Val Lys Asp Asn
        195                 200                 205 gca gga aaa att aaa cca tcc ttc aat ata gtg cct tta act tcc cgt    732
Ala Gly Lys Ile Lys Pro Ser Phe Asn Ile Val Pro Leu Thr Ser Arg
    210                 215                 220 gtg aaa cct gat cct cca cat att aaa aac ctc tcc ttc cac aat gat    780
Val Lys Pro Asp Pro Pro His Ile Lys Asn Leu Ser Phe His Asn Asp
225                 230                 235                 240 gac cta tat gtg caa tgg gag aat cca cag aat ttt att agc aga tgc    828
Asp Leu Tyr Val Gln Trp Glu Asn Pro Gln Asn Phe Ile Ser Arg Cys
                245                 250                 255 cta ttt tat gaa gta gaa gtc aat aac agc caa act gag aca cat aat    876
Leu Phe Tyr Glu Val Glu Val Asn Asn Ser Gln Thr Glu Thr His Asn
            260                 265                 270 gtt ttc tac gtc caa gag gct aaa tgt gag aat cca gaa ttt gag aga    924
Val Phe Tyr Val Gln Glu Ala Lys Cys Glu Asn Pro Glu Phe Glu Arg
        275                 280                 285 aat gtg gag aat aca tct tgt ttc atg gtc cct ggt gtt ctt cct gat    972
Asn Val Glu Asn Thr Ser Cys Phe Met Val Pro Gly Val Leu Pro Asp
    290                 295                 300
```

-continued

```
act ttg aac aca gtc aga ata aga gtc aaa aca aat aag tta tgc tat      1020
Thr Leu Asn Thr Val Arg Ile Arg Val Lys Thr Asn Lys Leu Cys Tyr
305                 310                 315                 320 gag gat gac aaa ctc tgg agt aat tgg agc caa gaa atg agt ata ggt      1068
Glu Asp Asp Lys Leu Trp Ser Asn Trp Ser Gln Glu Met Ser Ile Gly
                325                 330                 335 aag aag cgc aat tcc aca ctc tac ata acc atg tta ctc att gtt cca      1116
Lys Lys Arg Asn Ser Thr Leu Tyr Ile Thr Met Leu Leu Ile Val Pro
            340                 345                 350 gtc atc gtc gca ggt gca atc ata gta ctc ctg ctt tac cta aaa agg      1164
Val Ile Val Ala Gly Ala Ile Ile Val Leu Leu Leu Tyr Leu Lys Arg
        355                 360                 365 ctc aag att att ata ttc cct cca att cct gat cct ggc aag att ttt      1212
Leu Lys Ile Ile Ile Phe Pro Pro Ile Pro Asp Pro Gly Lys Ile Phe
    370                 375                 380 aaa gaa atg ttt gga gac cag aat gat gat act ctg cac tgg aag aag      1260
Lys Glu Met Phe Gly Asp Gln Asn Asp Asp Thr Leu His Trp Lys Lys
385                 390                 395                 400 tac gac atc tat gag aag caa acc aag gag gaa acc gac tct gta gtg      1308
Tyr Asp Ile Tyr Glu Lys Gln Thr Lys Glu Glu Thr Asp Ser Val Val
                405                 410                 415 ctg ata gaa aac ctg aag aaa gcc tct cag tgatggagat aatttatttt        1358
Leu Ile Glu Asn Leu Lys Lys Ala Ser Gln
            420                 425 taccttcact gtgaccttga gaaga                                          1383
```

<210> SEQ ID NO 4
<211> LENGTH: 426
<212> TYPE: PRT
<213> ORGANISM: human

<400> SEQUENCE: 4

```
Met Glu Trp Pro Ala Arg Leu Cys Gly Leu Trp Ala Leu Leu Leu Cys
1               5                   10                  15

Ala Gly Gly Gly Gly Gly Gly Gly Ala Pro Thr Glu Thr Gln Pro
            20                  25                  30

Pro Val Thr Asn Leu Ser Val Ser Val Glu Asn Leu Cys Thr Val Ile
        35                  40                  45

Trp Thr Trp Asn Pro Pro Glu Gly Ala Ser Ser Asn Cys Ser Leu Trp
    50                  55                  60

Tyr Phe Ser His Phe Gly Asp Lys Gln Asp Lys Lys Ile Ala Pro Glu
65                  70                  75                  80

Thr Arg Arg Ser Ile Glu Val Pro Leu Asn Glu Arg Ile Cys Leu Gln
                85                  90                  95

Val Gly Ser Gln Cys Ser Thr Asn Glu Ser Glu Lys Pro Ser Ile Leu
            100                 105                 110

Val Glu Lys Cys Ile Ser Pro Pro Glu Gly Asp Pro Glu Ser Ala Val
        115                 120                 125

Thr Glu Leu Gln Cys Ile Trp His Asn Leu Ser Tyr Met Lys Cys Ser
    130                 135                 140

Trp Leu Pro Gly Arg Asn Thr Ser Pro Asp Thr Asn Tyr Thr Leu Tyr
145                 150                 155                 160

Tyr Trp His Arg Ser Leu Glu Lys Ile His Gln Cys Glu Asn Ile Phe
                165                 170                 175

Arg Glu Gly Gln Tyr Phe Gly Cys Ser Phe Asp Leu Thr Lys Val Lys
            180                 185                 190
```

-continued

```
Asp Ser Ser Phe Glu Gln His Ser Val Gln Ile Met Val Lys Asp Asn
        195                 200                 205

Ala Gly Lys Ile Lys Pro Ser Phe Asn Ile Val Pro Leu Thr Ser Arg
        210                 215                 220

Val Lys Pro Asp Pro Pro His Ile Lys Asn Leu Ser Phe His Asn Asp
225                 230                 235                 240

Asp Leu Tyr Val Gln Trp Glu Asn Pro Gln Asn Phe Ile Ser Arg Cys
                245                 250                 255

Leu Phe Tyr Glu Val Glu Val Asn Asn Ser Gln Thr Glu Thr His Asn
            260                 265                 270

Val Phe Tyr Val Gln Glu Ala Lys Cys Glu Asn Pro Glu Phe Glu Arg
            275                 280                 285

Asn Val Glu Asn Thr Ser Cys Phe Met Val Pro Gly Val Leu Pro Asp
        290                 295                 300

Thr Leu Asn Thr Val Arg Ile Arg Val Lys Thr Asn Lys Leu Cys Tyr
305                 310                 315                 320

Glu Asp Asp Lys Leu Trp Ser Asn Trp Ser Gln Met Ser Ile Gly
                325                 330                 335

Lys Lys Arg Asn Ser Thr Leu Tyr Ile Thr Met Leu Leu Ile Val Pro
                340                 345                 350

Val Ile Val Ala Gly Ala Ile Ile Val Leu Leu Leu Tyr Leu Lys Arg
            355                 360                 365

Leu Lys Ile Ile Ile Phe Pro Pro Ile Pro Asp Pro Gly Lys Ile Phe
        370                 375                 380

Lys Glu Met Phe Gly Asp Gln Asn Asp Asp Thr Leu His Trp Lys Lys
385                 390                 395                 400

Tyr Asp Ile Tyr Glu Lys Gln Thr Lys Glu Glu Thr Asp Ser Val Val
                405                 410                 415

Leu Ile Glu Asn Leu Lys Lys Ala Ser Gln
        420                 425
```

```
<210> SEQ ID NO 5
<211> LENGTH: 30
<212> TYPE: PRT
<213> ORGANISM: artificial sequence
<220> FEATURE:
<223> OTHER INFORMATION: signal sequence of murine IL-3

<400> SEQUENCE: 5

Met Val Leu Ala Ser Ser Thr Thr Ser Ile His Thr Met Leu Leu Leu
1               5                   10                  15

Leu Leu Met Leu Phe His Leu Gly Leu Gln Ala Ser Ile Ser
            20                  25                  30

<210> SEQ ID NO 6
<211> LENGTH: 8
<212> TYPE: PRT
<213> ORGANISM: artificial sequence
<220> FEATURE:
<223> OTHER INFORMATION: N-terminal FLAG epitope-tag

<400> SEQUENCE: 6

Asp Tyr Lys Asp Asp Asp Asp Lys
1               5

<210> SEQ ID NO 7
<211> LENGTH: 31
<212> TYPE: DNA
<213> ORGANISM: artificial sequence
```

```
<220> FEATURE:
<223> OTHER INFORMATION: Oligo 1478 5'

<400> SEQUENCE: 7
agcttctaga acagaagttc agccacctgt g                               31

<210> SEQ ID NO 8
<211> LENGTH: 30
<212> TYPE: DNA
<213> ORGANISM: artificial sequence
<220> FEATURE:
<223> OTHER INFORMATION: Oligo 1480 5'

<400> SEQUENCE: 8
aactccacct tctacaccac ctgatctaga                                 30

<210> SEQ ID NO 9
<211> LENGTH: 5
<212> TYPE: PRT
<213> ORGANISM: unknown
<220> FEATURE:
<223> OTHER INFORMATION: NR4 motif
<220> FEATURE:
<221> NAME/KEY: MISC_FEATURE
<222> LOCATION: (3)..(3)
<223> OTHER INFORMATION: X may be any amino acid

<400> SEQUENCE: 9

Trp Ser Xaa Trp Ser
1               5

<210> SEQ ID NO 10
<211> LENGTH: 27
<212> TYPE: PRT
<213> ORGANISM: unknown
<220> FEATURE:
<223> OTHER INFORMATION: N-terminal amino acid seuqence of mNR4 (major)
<220> FEATURE:
<221> NAME/KEY: MISC_FEATURE
<222> LOCATION: (24)..(24)
<223> OTHER INFORMATION: X may be any amino acid

<400> SEQUENCE: 10

Asp Tyr Lys Asp Asp Asp Tyr Lys Asp Asp Asp Glu Ser Arg Thr
1               5                   10                  15

Glu Val Gln Pro Pro Val Thr Xaa Leu Ser Val
            20                  25

<210> SEQ ID NO 11
<211> LENGTH: 27
<212> TYPE: PRT
<213> ORGANISM: unknown
<220> FEATURE:
<223> OTHER INFORMATION: N-terminal amino acid seqence of mNR4 (minor)
<220> FEATURE:
<221> NAME/KEY: MISC_FEATURE
<222> LOCATION: (24)..(24)
<223> OTHER INFORMATION: X may be any amino acid

<400> SEQUENCE: 11

Ala Ser Ile Ser Ser Ser Asp Tyr Lys Asp Asp Asp Glu Ser Arg Thr
1               5                   10                  15

Glu Val Gln Pro Pro Val Thr Xaa Leu Ser Val
            20                  25

<210> SEQ ID NO 12
<211> LENGTH: 5
```

```
<212> TYPE: PRT
<213> ORGANISM: unknown
<220> FEATURE:
<223> OTHER INFORMATION: peptide motif found in many members of the
      haemopoietin receptor family

<400> SEQUENCE: 12

Trp Ser Asp Trp Ser
1               5
```

HAEMOPOIETIN RECEPTOR AND GENETIC SEQUENCES ENCODING SAME

CROSS REFERENCE TO RELATED APPLICATIONS

The present application is a divisional of application Ser. No. 09/051,843 filed Oct. 23, 1996, which is a 371 of PCT/AU96/00668 filed Oct. 23, 1998.

FIELD OF THE INVENTION

The present invention relates generally to a novel haemopoietin receptor or components or parts thereof and to genetic sequences encoding same. The receptor molecules and their components and/or parts and the genetic sequences encoding same of the present invention are useful in the development of a wide range of agonists, antagonists, therapeutics and diagnostic reagents based on ligand interaction with its receptor.

BACKGROUND OF THE INVENTION

Bibliographic details of the publications numerically referred to in this specification are collected at the end of the description. Sequence Identity Numbers (SEQ ID NOs.) for the nucleotide and amino acid sequences referred to in the specification are defined following the bibliography.

Throughout this specification and the claims which follow, unless the context requires otherwise, the word "comprise", or variations such as "comprises" or "comprising", will be understood to imply the inclusion of a stated integer or group of integers but not the exclusion of any other integer or group of integers.

The preferred haempoietin receptor of the present invention is referred to herein as "NR4". The NR4 receptor interacts with IL-13 and is referred to herein as the EL-13 receptor or more particularly the IL-13 receptor α-chain (IL-13Rα). These terms are used interchangeably throughout the subject specification. The species from which a particular NR4 is derived is given in single letter abbreviation. For example, murine is "M" and human is "H". A recombinant form may have the prefix "r".

The rapidly increasing sophistication of recombinant DNA techniques is greatly facilitating research into the medical and allied health fields. Cytokine research is of particular importance, especially as these molecules regulate the proliferation, differentiation and function of a wide variety of cells. Administration of recombinant cytokines or regulating cytokine function and/or synthesis is increasingly becoming the focus of medical research into the treatment of a range of disease conditions.

Despite the discovery of a range of cytokines and other secreted regulators of cell function, comparatively few cytokines are directly used or targeted in therapeutic regimes. One reason for this is the pleiotropic nature of many cytokines. For example, interleukin (IL)-11 is a functionally pleiotropic molecule (1,2), initially characterized by its ability to stimulate proliferation of the IL-6-dependent plasmacytoma cell line, T11 65 (3). Other biological actions of IL-11 include induction of multipotential haemopoietin progenitor cell proliferation (4,5,6), enhancement of megakaryocyte and platelet formation (7,8,9,10), stimulation of acute phase protein synthesis (11) and inhibition of adipocyte lipoprotein lipase activity (12, 13).

Interleukin-13 (IL-13) is another important cytokine which shares a number of structural characteristics with interleukin-4 (IL-4) [reviewed in 14 and 15]. The genes for IL-4 and IL-13 have a related intron/exon structure and are located close together on chromosome 5 in the human and the syntenic region of chromosome 11 in the mouse (14, 15). At the protein level, IL-4 and IL-13 share approximately 30% amino acid identity, including four cysteine residues. Biologically, IL-13 and IL-4 are also similar, being produced by activated T-cells and acting upon, for example, macrophages to induce differentiation and suppress the production of inflammatory cytokines. Additionally, human IL-13 may act as a co-stimulatory signal for B-cell proliferation and affect immunoglobulin isotype switching (14, 15). The diverse and pleiotropic function of IL-13 and other haemopoietic cytokines makes this group important to study, especially at the level of interaction of the cytokine with its receptors. Manipulation and control of cytokine receptors and of cytokine-receptor interaction is potentially very important in many therapeutic situations, especially where the target cytokine is functionally pleiotropic and it is desired to block certain functions of a target cytokine but not all functions.

Research into IL-13 and its receptor has been hampered due to the inability to clone genetic sequences encoding all or part of the IL-13 receptor. In accordance with the present invention, genetic sequences have now been cloned encoding the IL-13 receptor α-chain, a receptor subunit which is also shared with the IL-4 receptor. The availability of these genetic sequences permits the development of a range of therapeutic and diagnostic agents capable of modulating or monitoring IL-13 activity as well as the activity of cytokines related to IL-13 at the level of structure or function. In accordance with the present invention, an example of a cytokine related in structure and function to IL-13 is IL-4.

SUMMARY OF THE INVENTION

Accordingly, one aspect of the present invention is directed to a nucleic acid molecule comprising a sequence of nucleotides encoding or complementary to a sequence encoding an haemopoietin receptor from an animal or a derivative of said receptor.

More particularly, the present invention provides an isolated nucleic acid molecule comprising a sequence of nucleotides encoding or complementary to a sequence encoding an animal haempoietin receptor or a derivative thereof, said receptor capable of interaction with IL-13 or a derivative of IL-13.

In a related embodiment, the present invention provides an isolated nucleic acid molecule comprising a sequence of nucleotides encoding or complementary to a sequence encoding an animal haempoietin receptor or a derivative thereof, wherein said receptor:

(i) is capable of interaction with IL-13 or its derivatives; and
(ii) is capable of interaction with a complex between IL-4 and IL-4 receptor α-chain.

In accordance with these embodiments, a derivative of IL-13 includes agonists, antagonists, antibodies and mimetics.

The present invention is also directed to a nucleic acid molecule comprising a sequence of nucleotides encoding or complementary to a sequence encoding an animal IL-13 receptor α-chain or a derivative thereof.

In a related embodiment, the present invention contemplates a nucleic acid molecule comprising a sequence of nucleotides encoding or complementary to a sequence encoding a component of an animal IL-4 receptor or a derivative thereof.

Preferably, the animal is a mammal or a species of bird. Particularly, preferred animals include humans, laboratory test animals (e.g. primates, mice, rabbits, hamsters, guinea pigs), livestock animals (e.g. sheep, goats, horses, pigs, cows, donkeys), companion animals (e.g. dogs cats), captive wild animals (e.g. foxes, kangaroos, dingoes) and poultry birds (e.g. chickens, geese, ducks) and game birds (e.g. emus, ostriches). Although the present invention is exemplified with respect to mice and humans, the scope of the subject invention extends to all animals and birds.

DETAILED DESCRIPTION OF THE INVENTION

The present invention is predicated in part on an ability to identify members of the haemopoietin receptor family on the basis of sequence similarity. Based on this approach, a genetic sequence was identified in accordance with the present invention which encodes a haemopoitin receptor. The expressed genetic sequence is referred to herein as "NR4". In accordance with the present invention, NR4 has an apparent molecular mass when synthesised by transfected COS cells of from about 50,000 to about 70,000 daltons, and more preferably from about 55,000 to about 65,000 daltons. NR4 binds to IL-13 specifically and with low affinity and is considered, therefore, to be an IL-13 receptor α-chain. Accordingly, the terms "NR4" and "IL-13 receptor α-chain" (or "IL-13 Rα") are used interchangeably throughout the subject specification. Furthermore, IL-13 binding to its receptor has been found to be competitively inhibited by IL-4 or a component thereof in cells which express the IL-4 receptor α-chain and this may provide a method for controlling IL-13-receptor interaction and will also provide a basis for the preparation and construction of mimetics.

Another aspect of the present invention provides a nucleic acid molecule comprising a sequence of nucleotides encoding IL-13 receptor α-chain having an amino acid sequence as set forth in SEQ ID NO:2 or having at least about 50% similarity to all or part thereof. Preferably, the percentage similarity is at least about 60%, more preferably at least about 70%, even more preferably at least about 80–85% and still even more preferably at least about 90–95% or greater. The reference to all or part of a sequence is intended to include defining a hybrid molecule comprising parts of two receptors. It is not intended to encompass single amino acids.

A further embodiment of the present invention contemplates a nucleic acid molecule comprising a sequence of nucleotides encoding the IL-13 receptor α-chain and having a nucleotide sequence substantially as set forth in SEQ ID NO:1 or having at least about 50% similarity to all or part thereof. Preferably, the percentage similarity is at least about 60%, more preferably at least about 70%, even more preferably at least about 80–85% and still even more preferably at least about 90–95% or greater.

Still another aspect of the present invention provides a nucleic acid molecule comprising a sequence of nucleotides encoding IL-13 receptor α-chain having an amino acid sequence as set forth in SEQ ID NO:4 or having at least about 50% similarity to all or part thereof. Preferably, the percentage similarity is at least about 60%, more preferably at least about 70%, even more preferably at least about 80–85% and still even more preferably at least about 90–95% or greater.

Yet still a further embodiment of the present invention contemplates a nucleic acid molecule comprising a sequence of nucleotides encoding the IL-13 receptor α-chain and having a nucleotide sequence substantially as set forth in SEQ ID NO:3 or having at least about 50% similarity to all or part thereof. Preferably, the percentage similarity is at least about 60%, more preferably at least about 70%, even more preferably at least about 80–85% and still even more preferably at least about 90–95% or greater.

Accordingly, the present invention extends to the sequence of nucleotides set forth in SEQ ID NO:1 or 3 or the sequence of amino acids set forth in SEQ ID NO:2 or 4 or single or multiple nucleotide or amino acid substitutions, deletions and/or additions thereto.

The present invention further extends to nucleic acid molecules capable of hybridising under low stringency conditions to the nucleotide sequence set forth in SEQ ID NO:1 or 3 or a complementary form thereof.

The present invention extends to recombinant haempoietin receptors and in particular recombinant NR4 and recombinant hybrids containing NR4. Preferred recombinant polypeptides interact with IL-13 with low affinity and even more preferably with high affinity.

In a particularly preferred embodiment polypeptide has at least two of the following characteristics:

(i) comprises an amino acid sequence substantially as set forth in SEQ ID NO:2 or SEQ ID NO:4 or having at least about 50% similarity to all or part thereof;

(ii) is encoded by a nucleotide sequence substantially as set forth in SEQ ID NO:1 or SEQ ID NO:3 or having at least about 50% similarity to all or part thereof;

(iii) interacts with IL-13 or its derivatives with at least low affinity; and (iv) has a molecular weight of from about 50,000 to about 70,000 daltons as determined by Western blot analysis when expressed in COS cells.

In a related embodiment, the polypeptide has at least three of the following characteristics:

(i) comprises an amino acid sequence substantially as set forth in SEQ ID NO:2 or SEQ ID NO:4 or having at least about 50% similarity to all or part thereof;

(ii) is encoded by a nucleotide sequence substantially as set forth in SEQ ID NO:1 or SEQ ID NO:3 or having at least about 50% similarity to all or part thereof;

(iii) interacts with IL-13 or its derivatives with at least low affinity;

(iv) has a molecular weight of from about 50,000 to about 70,000 daltons as determined by Western blot analysis when expressed in COS cells;

(v) comprises an amino acid sequence derived from IL-4 receptor α-chain; and (vi) is capable of interaction with IL-13 which is competitively inhibited by IL-4 in cells which express an IL-4 receptor α-chain.

Reference herein to "recombinant haempoietin receptor", "NR4", "IL-13 receptor" or "IL-13" receptor α-chain" includes reference to derivatives thereof such as parts, fragments, portions, homologues, hybrids or analogues thereof. The derivatives may be functional or not or may be non-functional but immunologically interactive with antibodies to all or part of the receptor. Derivatives of the receptor also cover agonists or antagonists of receptor-ligand interaction. Function is conveniently defined by an ability of NR4 to interact with IL-13 or its derivatives or for soluble NR4 to compete with IL-13-induced activities of certain cells.

Particularly preferred derivatives contemplated by the present invention include derivatives of IL-13 receptor α-chain which are capable of binding IL-13 with high affinity or with IL-13 and IL-4 with high affinity; derivatives also encompass chimeric molecules such as between IL-13 receptor α-chain and, for example, IL-4 receptor α-chain which also bind IL-13 with high affinity.

Other fusion or chimeric molecules contemplated by the present invention include those between NR4 and members of the haemopietin receptor family, receptor tyrosine kinases, TNF/NGF receptors and G protein-coupled receptors. For example, chimeras may be between NR-4 and IL-13 binding protein, IL-4 receptor α-chain, IL-2 receptor γ-chain or receptors for other cytokines involved or implicated in asthma and allergy such as IL-5. Other important chimeras include NR4 and immunoglobulins or other molecules which allow targeting of NR4 to particular cells or tissues, NR4 and toxins and NR4 and growth factors.

Reference herein to a low stringency at 42° C. includes and encompasses from at least about 1% v/v to at least about 15% v/v formamide and from at least about 1M to at least about 2M salt for hybridisation, and at least about 1M to at least about 2M salt for washing conditions. Alterative stringency conditions may be applied where necessary, such as medium stringency, which includes and encompasses from at least about 16% v/v to at least about 30% v/v formamide and from at least about 0.5M to at least about 0.9M salt for hybridisation, and at least about 0.5M to at least about 0.9M salt for washing conditions, or high stringency, which includes and encompasses from at least about 31% v/v to at least about 50% v/v formamide and from at least about 0.01M to at least about 0.15M salt for hybridisation, and at least about 0.01M to at least about 0.15M salt for washing conditions.

Yet another aspect of the present invention provides a nucleic acid molecule comprising a sequence of nucleotides which encodes or is complementary to a sequence which encodes an IL-13 receptor α-chain, said nucleic acid molecule having a nucleotide sequence substantially as set forth in SEQ ID NO:1 or 3 or a nucleic acid molecule which encodes a structurally similar IL-13 receptor α-cliain or a derivative thereof and which is capable of hybridising to the nucleotide sequence substantially as set forth in SEQ ID NO:1 or 3 or a complementary form thereof under low stringency conditions.

Still yet another aspect of the present invention is directed to a nucleic acid molecule comprising a sequence of nucleotides which encodes or is complementary to a sequence which encodes the IL-13 receptor α-chain having an amino acid sequence substantially as set forth in SEQ ID NO:2 or 4 or comprises a nucleotide sequence coding for an amino acid sequence having at least about 50% similarity to the sequence set forth in SEQ ID NO:2 or 4 and is capable of hybridising to the sequence set forth in SEQ ID NO:1 or 3 under low stringency conditions.

The nucleic acid molecules contemplated by the present invention are generally in isolated form and may be single or double stranded, linear or closed circle DNA (e.g. genomic DNA), cDNA or mRNA or combinations thereof such as in the form of DNA:RNA hybrids. In a particularly preferred embodiment, the nucleic acid molecules are in vectors and most preferably expression vectors to enable expression in a suitable host cell. Particularly useful host cells include prokaryotic cells, mammalian cells, yeast cells and insect cells. The cells may also be in the form of a cell line.

According to this aspect of the present invention there is provided an expression vector comprising a nucleic acid molecule encoding the IL-13 receptor α-chain as hereinbefore described, said expression vector capable of expression in a particular host cell.

Another aspect of the present invention contemplates a recombinant polypeptide comprising a sequence of amino acids substantially as set forth in SEQ ID NO:2 or 4 or having at least about 50% similarity to all or part thereof. Preferably, the percentage similarity is at least about 60%, more preferably at least about 70%, even more preferably at least about 80–85% and still even more preferably at least about 90–95% or greater.

The recombinant polypeptide contemplated by the present invention includes, therefore, components, parts, fragments, derivatives, homologues or analogues of the IL-13 receptor α-chain and is preferably encoded by a nucleotide sequence substantially set forth in SEQ ID NO:1 or 3 or a molecule having at least about 50% similarity to all or part thereof or a molecule capable of hybridising to the nucleotide sequence set forth in SEQ ID NO:1 or 3 or a complementary form thereof The recombinant molecule may be glycosylated or non-glycosylated. When in glycosylated form, the glycosylation may be substantially the same as naturally occurring IL-13 receptor α-chain or may be a modified form of glycosylation. Altered or differential glycosylation states may or may not affect binding activity of the IL-13 receptor α-chain.

The recombinant IL-13 receptor α-chain may be in soluble form or may be expressed on a cell surface or conjugated or fused to a solid support or another molecule.

The present invention further contemplates a method for producing a recombinant polypeptide having at least two of the following characteristics:

(i) comprises an amino acid sequence substantially as set forth in SEQ ID NO:2 or SEQ ID NO:4 or having at least about 50% similarity thereto;

(ii) is encoded by a nucleotide sequence substantially as set forth in SEQ ID NO:1 or SEQ ID NO:3 or having at least about 50% similarity thereto;

(iii) interacts with IL-13 or its derivatives with at least low affinity; and (iv) has a molecular weight of from about 50,000 to about 70,000 daltons as determined by Western blot analysis when expressed in COS cells, said method comprising culturing cells comprising the genetic constructs of the present invention for a time and under conditions sufficient to express the nucleic acid molecule in said genetic construct to produce a recombinant polypeptide and isolating said recombinant polypeptide.

Another embodiment provides a method of producing a recombinant polypeptide having at least three of the following characteristics:

(i) comprises an amino acid sequence substantially as set forth in SEQ ID NO:2 or SEQ ID NO:4 or having at least about 50% similarity to all or part thereof;

(ii) is encoded by a nucleotide sequence substantially as set forth in SEQ ID NO:1 or SEQ ID NO:3 or having at least about 50% similarity to all or part thereof;

(iii) interacts with IL-13 or its derivatives with at least low affinity;

(iv) has a molecular weight of from about 50,000 to about 70,000 daltons as determined by Western blot analysis when expressed in COS cells;

(v) comprises an amino acid sequence derived from IL-4 receptor α-chain; and (vi) is capable of interaction with IL-13 which is competitively inhibited by IL-4 in cells which express an IL-4 receptor α-chain.

said method comprising culturing cells comprising the fusion genetic constructs according to the present invention for a time and under conditions sufficient to express the nucleic acid molecule in said fusion genetic constructs to produce a recombinant polypeptide and isolating said recombinant polypeptide.

The present invention further extends to cells such as animal cells which express the above-mentioned recombinant polypeptides.

Another embodiment of the present invention provides chemical analogues of the recombinant IL-13 receptor α-chain.

As stated above, the present invention further contemplates a range of derivatives of NR4. Derivatives include fragments, parts, portions, mutants, hybrids (including fusion and chimeric molecules), homologues and analogues of the NR4 polypeptide and corresponding genetic sequence. In one preferred embodiment, the derivatives bind IL-13 with high affinity. Other preferred derivatives act as agonists, antagonist or mimetics. Derivatives also include single or multiple amino acid substitutions, deletions and/or additions to NR4 or single or multiple nucleotide substitutions, deletions and/or additions to the genetic sequence encoding NR4. "Additions" to amino acid sequences or nucleotide sequences include fusions with other peptides, polypeptides or proteins or fusions to nucleotide sequences. Reference herein to "NR4" includes reference to all derivatives thereof including functional derivatives or "NR4" immunologically interactive derivatives. The present invention also extends to hybrid molecules, such as between murine or human NR4 or derivatives thereof. A particularly preferred hybrid comprises NR4 and IL-4 receptor α-chain.

Analogues of NR4 contemplated herein include, but are not limited to, modification to side chains, incorporating of unnatural amino acids and/or their derivatives during peptide, polypeptide or protein synthesis and the use of crosslinkers and other methods which impose conformational constraints on the proteinaceous molecule or their analogues.

Examples of side chain modifications contemplated by the present invention include modifications of amino groups such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2, 4, 6-trinitrobenzene sulphonic acid (TNBS); acylation of amino groups with succinic anhydride and tetrahydrophthalic anhydride; and pyridoxylation of lysine with pyridoxal-5-phosphate followed by reduction with $NaBH_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromedcuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

A Modification of the imidazole ring of a histidine residue may be accomplished by alkylation with iodoacetic acid derivatives or N-carbethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. A list of unnatural amino acid, contemplated herein is shown in Table 1.

Crosslinkers can be used, for example, to stabilise 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodijmide (COOH).

In addition, peptides can be conformationally constrained by, for example, incorporation of $C_\alpha$ and $N_\alpha$-methylamino acids, introduction of double bonds between $C_\alpha$ and $C_\beta$ atoms of amino acids and the formation of cyclic peptides or analogues by introducing covalent bonds such as forming an amide bond between the N and C termini, between two side chains or between a side chain and the N or C terminus.

These types of modifications may be important to stabilise NR4 if administered to an individual or for use as a diagnostic reagen The present invention further contemplates chemical analogues of NR4 capable of acting as antagonists or agonists of NR4 or which can act as functional analogues of NR4. Chemical analogues may not necessarily be derived from NR4 but may share certain conformational similarities. Alternatively, chemical analogues may be specifically designed to mimic certain physiochemical properties of NR4. Chemical analogues may be chemically synthesised or may be detected following, for example, natural product screening.

The identification of NR4 permits the generation of a range of therapeutic molecules capable of modulating expression of NR4 or modulating the activity of NR4. Modulators contemplated by the present invention includes agonists and antagonists of NR4 gene expression or NR4 protein activity. Antagonists of NR4 gene expression include antisense molecules, ribozymes and co-suppression molecules. Agonists include molecules which increase promoter ability or interfere with negative regulatory mechanisms. Agonists of NR4 protein include antibodies, ligands and mimetics. Antagonists of NR4 include antibodies and inhibitor peptide fragments. Where a cell co-expresses NR4 and IL-4 receptor α-chain, agonists and antagonists may target the IL-4 receptor α-chain.

TABLE 1

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylaspargine | Nma |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisoleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcylcopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylthistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl))glycine | Nser |
| D-N-methylisoleucine | Dnmile | N-(imidazolylethyl))glycine | Nhps |
| D-N-methylleucine | Dnmleu | N-(3-indolylyethyl)glycine | Nhtrp |
| D-N-methyllysine | Dnmys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenylalanine | Nmhpe |
| N-(N-(2,2-diphenylethyl)carbamylmethyl)glycine | Nnbhm | N-(N-(3,3-diphenylpropyl)carbamylmethyl)glycine | Nnbhe |
| 1-carboxy-1-(2,2-diphenylethylamino)-cyclopropane | Nmbc |  |  |

Other derivatives contemplated by the present invention include a range of glycosylation variants from a completely unglycosylated molecule to a modified glycosylated molecule. Altered glycosylation patterns may result from expression of recombinant molecules in different host cells.

Another embodiment of the present invention contemplates a method for modulating expression of the NR4 gene in a human, said method comprising contacting the NR4 gene encoding NR4 with an effective amount of a modulator of NR4 expression for a time and under conditions sufficient to up-regulate or down-regulate or otherwise modulate expression of NR4. A nucleic acid molecule encoding NR4 or a derivative thereof may also be introduced into a cell to enhance or alter NR4 related activities of that cell including replacing an endogenous NR4 gene sequence which may, for example, be defective or carry one or more undesired mutations. Conversely, NR4 antisense sequences (or sense sequences for co-suppression) such as oligonucleotides may be introduced to decrease NR4-related activies of any cell expressing the endogenous NR4 gene. Ribozymes may also be used.

Another aspect of the present invention contemplates a method of modulating activity of NR4 in a human, said method comprising administering to said mammal a modulating effective amount of a molecule for a time and under conditions sufficient to increase or decrease NR4 activity. The molecule may be a proteinaceous molecule or a chemical entity and may also be a derivative of NR4 or its ligand or a chemical analogue or truncation mutant of NR4 or its ligand.

For example, IL-13 and IL-4 have been impliciated in the modulation of immune responses and in the production of IgE which is the immunoglobulin isotype associated with allergic or atopic diseases such as asthma. Modulating interactions between IL-13/IL-4 and their receptors may be important in treating inflammatory conditions such as allergic conditions. Elevated levels of IL-4/IL-13 and IgE are also important in diseases such as nephrotic syndrome, vernal and keratoconjunctivitis. Other diseases, the treatment of which is contemplated herein include bronchial asthma, perennial rhinitis and atopic dermatitis. Other disease conditions for which modulation of IL-13-receptor interaction may be important includes those conditions where IL-13 induces cytokine formation which in turn are involved in onset, progression and/or severity of diseases. Similarly, modulating IL-4-receptor interaction may also be important in controlling disease conditions. For example, some cancers may be exacerbated by the cytokine IL-13 or IL-4 which induce repressive immune effects or effector molecules which in turn reduce the body's ability to respond to the growth of the cancers.

Accordingly, the present invention contemplates a pharmaceutical composition comprising NR4 or a derivative thereof or a modulator of NR4 expression or NR4 activity and one or more pharmaceutically acceptable carriers and/or diluents. These components are referred to as the "active ingredients".

In this regard there is provided a pharmaceutical composition comprising a recombinant haemopoietin receptor as hereinbefore described or a ligand (e.g. IL-13) binding portion thereof and one or more pharmaceutically acceptable carriers and/or diluents.

In another embodiment, there is provided a pharmaceutical composition comprising a ligand (e.g. IL-13) to the recombinant haemopoietin receptor as hereinbefore described and one or more pharmaceutically acceptable carriers and/or diluents.

Still a further aspect of the present invention contemplates a method of treatment of an animal comprising administering to said animal a treatment effective amount of a recombinant haemopoietin receptor as hereinbefore described or a ligand binding portion thereof or a ligand (e.g. IL-13) to said haempoictic receptor for a time and under conditions sufficient for said treatment to be substantially effected or the conditions to be substantially ameliorated.

The pharmaceutical forms suitable for injectable use include sterile aqueous solutions (where water soluble) or dispersions and sterile powders for die extemporaneous preparation of sterile injectable solutions or dispersion or may be in the form of a cream or other form suitable for topical application. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as licithin, by the maintenance of the required particle size in the case of dispersion and by the use of superfactants. The preventions of the action of microorganisms can be brought about by various antibacterial and antifungal agents, for example, parabens, chlorobutanol, phenol, sorbic acid, thirmerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof When the active ingredients are suitably protected they may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, anb the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions in such that a suitable dosage will be obtained. Preferred compositions or preparations according to the present invention are prepared so that an oral dosage unit form contains between about 0.1 ug and 2000 mg of active compound.

The tablets, troches, pills, capsules and the like may also contain the components as listed hereafter: A binder such as gum, acacia, corn starch or gelatin; excipients such as dicalcium phosphate; a disintegrating agent such as corn starch, potato starch, algiaic acid and the like; a lubricant such as magnesium stearate; and a sweetening agent such a sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound(s) may be incorporated into sustained-release preparations and formulations.

The present invention also extends to forms suitable for topical application such as creams, lotions and gels.

Pharmaceutically acceptable carriers and/or diluents include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary activd ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from 0.5 $\mu$g to about 2000 mg. Expressed in proportions, the active compound is generally present in from about 0.5 $\mu$g to about 2000 mg/ml of carrier. In the case of compositions containing supplementary active ingredients, the dosages are determined by reference to the usual dose and manner of administration of the said ingredients.

The pharmaceutical composition may also comprise genetic molecules such as a vector capable of transfecting target cells where the vector carries a nucleic acid molecule capable of modulating NR4 expression or NR4 activity. The vector may, for example, be a viral vector.

Still another aspect of the present invention is directed to antibodies to NR4 and its derivatives or its ligands (e.g. IL-13). Such antibodies may be monoclonal or polyclonal and may be selected from naturally occurring antibodies to NR4 or may be specifically raised to NR4 or derivatives thereof. In the case of the latter, NR4 or its derivatives may first need to be associated with a carrier molecule. The antibodies and/or recombinant NR4 or its derivatives of the present invention are particularly useful as therapeutic or diagnostic agents.

For example, NR4 and its derivatives can be used to screen for naturally occurring antibodies to NR4. These may occur, for example in some autoimmune diseases. Alternatively, specific antibodies can be used to screen for NR4. Techniques for such assays are well known in the art and include, for example, sandwich assays and ELISA Knowledge of NR4 levels and/or IL-13 levels may be important for diagnosis of certain cancers or a predisposition to cancers or for monitoring certain therapeutic protocols. In particular, it may be important to monitor an IgE response or levels of IL-13 or IL-4 or both which in turn have an effect on the immune system.

Antibodies to NR4 of the present invention may be monoclonal or polyclonal. Alternatively, fragments of antibodies may be used such as Fab fragments. Furthermore, the present invention extends to recombinant and synthetic antibodies and to antibody hybrids. A "synthetic antibody" is considered herein to include fragments and hybrids of antibodies. The antibodies of this aspect of the present invention are particularly useful for immunotherapy and may also be used as a diagnostic tool for assessing the receptor or receptor-ligand interaction or monitoring the program of a therapeutic regimin.

For example, specific antibodies can be used to screen for NR4 proteins. The latter would be important, for example, as a means for screening for levels of NR4 in a cell extract or other biological fluid or purifying NR4 made by recombinant means from culture supernatant fluid. Techniques for the assays contemplated herein are known in the art and include, for example, sandwich assays and ELISA.

It is within the scope of this invention to include any second antibodies (monoclonal, polyclonal or fragments of antibodies or synthetic antibodies) directed to the first mentioned antibodies discussed above. Both the first and second antibodies may be used in detection assays or a first antibody may be used with a commercially available anti-immunoglobulin antibody. An antibody as contemplated herein includes any antibody specific to any region of NR4.

Both polyclonal and monoclonal antibodies are obtainable by immunization with the receptor and either type is utilizable for imnmunoassays. The methods of obtaining both types of sera are well known in the art. Polyclonal sera are less preferred but are relatively easily prepared by injection of a suitable laboratory animal with an effective amount of NR4, or antigenic parts thereof, collecting serum from the animal, and isolating specific sera by any of the known immunoadsorbent techniques. Although antibodies produced by this method are utilizable in virtually any type of immunoassay, they are generally less favoured because of the potential heterogeneity of the product.

The use of monoclonal antibodies in an immunoassay is particularly preferred because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are well known to those who are skilled in the art.

Another aspect of the present invention contemplates a method for detecting NR4 in a biological sample from a subject said method comprising contacting said biological sample with an antibody specific for NR4 or its derivatives or homologues for a time and under conditions sufficient for an antibody-NR4 complex to form, and then detecting said complex.

The presence of NR4 may be accomplished in a number of ways such as by Western blotting and ELISA procedures. A wide range of immunoassay techniques are available as can be seen by reference to U.S. Pat. Nos. 4,016,043, 4,424,279 and 4,018,653. These, of course, include both single-site and two-site or "sandwich" assays of the non-competitive types, as well as in the traditional competitive binding assays. These assays also include direct binding of a labelled antibody to a target.

Sandwich assays are among the most useful and commonly used assays and are favoured for use in the present invention. A number of variations of the sandwich assay technique exist, and all are intended to be encompassed by the present invention. Briefly, in a typical forward assay, an unlabelled antibody is immobilized on a solid substrate and the sample to be tested brought into contact with the bound molecule. After a suitable period of incubation, for a period of time sufficient to allow formation of an antibody-antigen complex, a second antibody specific to the antigen, labelled with a reporter molecule capable of producing a delectable signal is then added and incubated, allowing time sufficient for the formation of another complex of antibody-antigen-labelled antibody. Any unreacted material is washed away, and the presence of the antigen is determined by observation of a signal produced by the reporter molecule. The results may either be qualitative, by simple observation of the visible signal, or may be quantitated by comparing with a control sample containing known amounts of hapten. Variations on the forward assay include a simultaneous assay, in which both sample and labelled antibody are added simultaneously to the bound antibody. These techniques are well known to those skilled in the art, including any minor variations as will be readily apparent. In accordance with the present invention the sample is one which might contain NR4 including cell extact, tissue biopsy or possibly serum, saliva, mucosal secretions, lymph, tissue fluid and respiratory fluid. The sample is, therefore, generally a biological sample comprising biological fluid, cell extract, bone marrow or lymph, tissue extract (e.g. from kidney, liver, spleen, etc), fermentation fluid and supernatant fluid such as from a cell culture and cell conditioned medium.

In the typical forward sandwich assay, a first antibody having specificity for the NR4 or antigenic parts thereof, is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well-known in the art and generally consist of cross-linking covalently binding or physically adsorbing, the polymer-antibody complex is washed in preparation for the test sample. An aliquot of the sample to be tested is then added to the solid phase complex and incubated for a period of time sufficient (e.g. 2–40 minutes) and under suitable conditions (e.g. 25° C.) to allow binding of any subunit present in the antibody. Following the incubation period, the antibody subunit solid phase is washed and dried and incubated with a second antibody specific for a portion of the hapten. The second antibody is linked to a reporter molecule which is used to indicate the binding of the second antibody to the hapten.

An alternative method involves immobilizing the target molecules in the biological sample and then exposing the immobilized target to specific antibody which may or may not be labelled with a reporter molecule. Depending on the amount of target and the strength of the reporter molecule signal, a bound target may be detectable by direct labelling with the antibody. Alternatively, a second labelled antibody, specific to the first antibody is exposed to the target-first antibody complex to form a target-first antibody-second antibody tertiary complex. The complex is detected by the signal emitted by the reporter molecule.

By "reporter molecule" as used in the present specification, is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores or radionuclide containing molecules (i.e. radioisotopes) and chemiluminescent molecules.

In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, beta-galactosidase and alkaline phosphatase, amongst others. The substrates to be used with the specific enzymes are generally chosen for the production, upon hydrolysis by the corresponding enzyme, of a detectable colour change. Examples of suitable enzymes include alkaline phosphatase and peroxidase. It is also possible to employ fluorogenic substrates, which yield a fluorescent product rather than the chromogenic substrates noted above. In all cases, the enzyme-labelled antibody is added to the first antibody hapten complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of hapten which was present in the sample. "Reporter molecule" also extends to use of cell agglutination or inhibition of agglutination such as red blood cells on latex beads, and the like.

Alternately, fluorescent compounds, such as fluorescein and rhodamine, may be chemically coupled to antibodies without altering their binding capacity. When activated by illumination with light of a particular wavelength, the fluorochrome-labelled antibody adsorbs the light energy, inducing a state to excitability in the molecule, followed by emission of the light at a characteristic colour visually detectable with a light microscope. As in the EIA, the fluorescent labelled antibody is allowed to bind to the first antibody-hapten complex. After washing off the unbound reagent, the remaining tertiary complex is then exposed to the light of the appropriate wavelength the fluorescence observed indicates the presence of the hapten of interest Immunofluorescene and EIA techniques are both very well established in the art and are particularly preferred for the present method. However, other reporter molecules, such as radioisotope, chemiluminescent or bioluminescent molecules, may also be employed.

Another form of assay involves cells capable of expressing NR4 and IL-4 receptor α-chain. For example, if IL-4 receptor α-chain and NR4 are co-expressed on cells, such as COS cells, then IL-13 binds to NR4 with a high affinity in the presence of IL4.

Although not intending to limit the present invention to any one theory or mode of action, when NR4 and the IL-4 receptor are expressed in the same cell, they contribute to the formation of both IL-4 and IL-13 receptors. In the case of IL-4, binding occurs first through the IL-4 receptor α-chain and then NR4 interacts with this complex. In the case of IL-13, binding occurs first to NR4 and then IL-4 receptor α-chain interacts with the complex to form a high affinity receptor capable of signal transduction. The consequences of co-expression of NR4 and IL-4 receptor α-chain is that IL-4 and IL-13 can compete with each other for binding to the IL-4 receptor α-chain and NR4.

Based on this behaviour, it would appear that any protein or small molecule that prevented IL-4 or IL-13 forming cell surface complexes containing both receptor components may be antagonistic. Such molecules may prevent interaction of the cytokine with its low affinity receptor. For example, soluble IL-13BP can prevent IL-13 interaction with NR4. Likewise, soluble IL-4 receptor α-chain can prevent binding of IL-4 to cell surface IL-4 receptor α-chain. These reagents would be antagonists that were specific for IL-4 or IL-13.

By extension, because of its very low affinity, soluble NR4 is a very inefficient IL-13 antagonist. If a soluble NR4 mutant is selected that now binds to IL-4 and also binds to IL-13 with higher affinity, this would be a useful antagonist of both IL-4 and IL-13.

An alternative to use of soluble receptor, is to generate a panel of monoclonal antibodies to NR4. If an antibody is obtained which prevents interaction of NR4 with the IL-4 receptor α-chain, a critical event in formation of both functional IL-4 receptor and functional IL-13 receptors, then again the action of both cytokines is inhibited.

In a one particular embodiment the present invention contemplates a method for monitoring the level of IL-4 in a biological sample said method comprising incubating said biological sample with cells which express NR4 and IL-4 receptor α-chain together with an effective amount of IL-13 to competitively inhibit IL-4 binding to its receptor and determining the extent of competitive inhibition.

In a related embodiment the present invention contemplates a method for monitoring the level of IL-13 in a biological sample said method comprising incubating said biological sample with cells which express NR4 and IL-4 receptor α-chain together with an effective amount of IL-4 to competitively inhibit IL-13 binding to its receptor and determining the extent of competitive inhibition.

Preferably, the cytokines are labelled with a reporter molecule as described above.

The biological sample includes but is not limited to blood, serum, plasma, tissue fluid, tissue extract, lymph, T cells or extracts thereof, culture supernatant and conditioned medium.

The present invention also contemplates genetic assays such as involving PCR analysis to detect NR4 gene or its derivatives. Alternative methods or methods used in conjunction include direct nucleotide sequencing or mutation scanning such as single stranded conformation polymorphisms analysis (SSCP) as specific oligonucleotide hybridisation, as methods such as direct protein truncation tests. Such genetic tests may be important, for example, in genetic screening of animals (e.g. humans) for non-expression or substantial absence of expression or expression of mutant forms of NR4 leading to disease conditions.

The nucleic acid molecules of the present invention may be DNA or RNA. When the nucleic acid molecule is in DNA form, it may oe genomic DNA or cDNA. RNA forms of the nucleic acid molecules of die present invention are generally mRNA.

Although the nucleic acid molecules of the present invention are generally in isolated form, they may be integrated into or ligated to or otherwise fused or associated with other genetic molecules such as vector molecules and in particular expression vector molecules. Vectors and expression vectors are generally capable of replication and, if applicable, expression in one or both of a prokaryotic cell or a eukaryotic cell. Preferably, prokaryotic cells include *E. coli*, *Bacillus* sp and *Pseudomonas* sp. Preferred eukaryotic cells include yeast, fungal, mammalian and insect cells.

Accordingly, another aspect of the present invention contemplates a genetic construct comprising a vector portion and a mammalian and more particularly a human NR4 gene portion, which NR4 gene portion is capable of encoding an NR4 polypeptide or a functional or immunologically interactive derivative thereof.

Preferably, the NR4 gene portion of the genetic construct is operably linked to a promoter on the vector such that said promoter is capable of directing expression of said NR4 gene portion in an appropriate cell.

In addition, the NR4 gene portion of the genetic construct may comprise all or part of the gene fused to another genetic sequence such as a nucleotide sequence encoding glutathione-S-transferase or part thereof or a cytokine or another haempoietic receptor. Hybrid receptor molecules are particularly useful in the development of multi functional therapeutic and diagnostic agents.

The present invention extends to such genetic constructs and to prokaryotic or eukaryotic cells comprising same.

The present invention also extends to any or all derivatives of NR4 including mutants, part, fragments, portions, homologues and analogues or their encoding genetic sequence including single or multiple nucleotide or amino acid substitutions, additions and/or deletions to the naturally occurring nucleotide or amino acid sequence.

The NR4 and its genetic sequence of the present invention will be useful in the generation of a range of therapeutic and diagnostic reagents and will be especially useful in the detection of a corresponding ligand. For example, recombinant NR4 may be bound or fused to a reporter molecule capable of producing an identifiable signal, contacted with a biological sample putatively containing a ligand and screening for binding of the labelled NR4 to the ligand. Alternatively, labelled NR4 may be used to screen expression libraries of putative ligand genes or functional parts thereof.

In another embodiment, the NR4 is first immobilised. According to this embodiment, there is provided a method comprising contacting a biological sample containing a putative ligand with said haempoietic receptor or a ligand binding portion thereof immobilised to a solid support for a time and under conditions sufficient for a complex to form between said receptor and said ligand if said ligand is present in said biological sample, eluting bound ligand and isolating same.

Soluble NR4 polypeptides as well as various hybrids are also contemplated to be useful in the treatment of disease, injury or abnormality in the nervous system, e.g. in relation to central or peripheral nervous system to treat Cerebral Palsy, trauma induced paralysis, vascular ischaemia associated with stroke, neuronal tumours, motoneurone disease, Parkinson's disease, Huntington's disease, Alzheimer's disease, Multiple Sclerosis, peripheral neuropathies associated with diabetes, heavy metal or alcohol toxicity, renal failure and infectious diseases such as herpes, rubella, measles, chicken pox, HIV or HTLV-1. The NR4 polypeptides and hybrids may also be important for regulating cytokine activity and/or modulating haempoiesis. They are also important for treating allergic or atopic conditions as well as other inflammatory conditions such as rheumatoid arthritis.

As stated above, the NR4 or its ligand of the present invention or their functional derivatives may be provided in a pharmaceutical composition together with one or more pharmaceutically acceptable carriers and/or diluents. In addition, the present invention contemplates a method of treatment comprising the administration of an effective amount of NR4 of the present invention. The present invention also extends to antagonists and agonists of NR4 and/or its ligand and their use in therapeutic compositions and methodologies.

A further aspect of the present invention contemplates the use of NR4 or its functional derivatives in tie manufacture of a medicament for the treatment of NR4 mediated conditions defective or deficient.

The present invention is further described by the following non-limiting Figures and Examples.

BRIEF DESCRIPTION OF THE DRAWINGS

FIGS. 7A–7J show the nucleotide and corresponding amino acid sequence of murine SEQ ID NOS: 1 and 2, respectively) and human (SEQ ID NOS: 3 and 4, respectively) NR4 (IL-13Rα) genes. The nucleotide and predicted amino acid sequence of human (H) and murine (M) IL-13Rα(NR4) were aligned by eye, with gaps (-) inserted to optimize the alignment. The numbering is for the murine clone, nucleotides that form part of the coding region are shown in upper case, whilst those of the untranslated regions are shown in lower case. Amino acids identical between the predicted murine and human proteins are indicated by (*). DNA encoding the murine signal sequence is underlined, with A26 or T27 being the predicted first amino acid of the mature protein.

The following single and three letter abbreviations for amino acid residues are used in the specification:

| Amino Acid | Three-letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any residue | Xaa | X |

EXAMPLE 1

Isolation of Genomic and cDNAs Encoding NR4

ApoI digested genomic DNA, extracted from an embryonal stem cell line, was cloned into the λZAPII bacteriophage (Stratagene, LaJolla, Calif.). Approximately $10^6$ plaques from this library were screened with a $^{32}$P-labelled oligonucleotide corresponding to the sequence Trp-Ser-Asp-Trp-Ser (16). Positively hybridising clones were sequenced using an automated DNA sequencer according to the manufacturer's instructions (Applied Biosystems, Foster City, Calif.). One clone appeared to encode for part of a new member of the haemopoietin receptor family. Oligonucleotides were designed on the basis of this genomic DNA sequence and were used in the conventional manner to isolate clones from mouse peritoneal macrophage (Clontech Laboratories, Palo Alto, Calif.), mouse skin, mouse lung, mouse kidney, and WEHI-3B. (Stratagene, LaJolla, Calif.) λ-bacteriophage cDNA libraries.

EXAMPLE 2

Construction of Expression Vectors and Transfection of Cells

Figure 1:
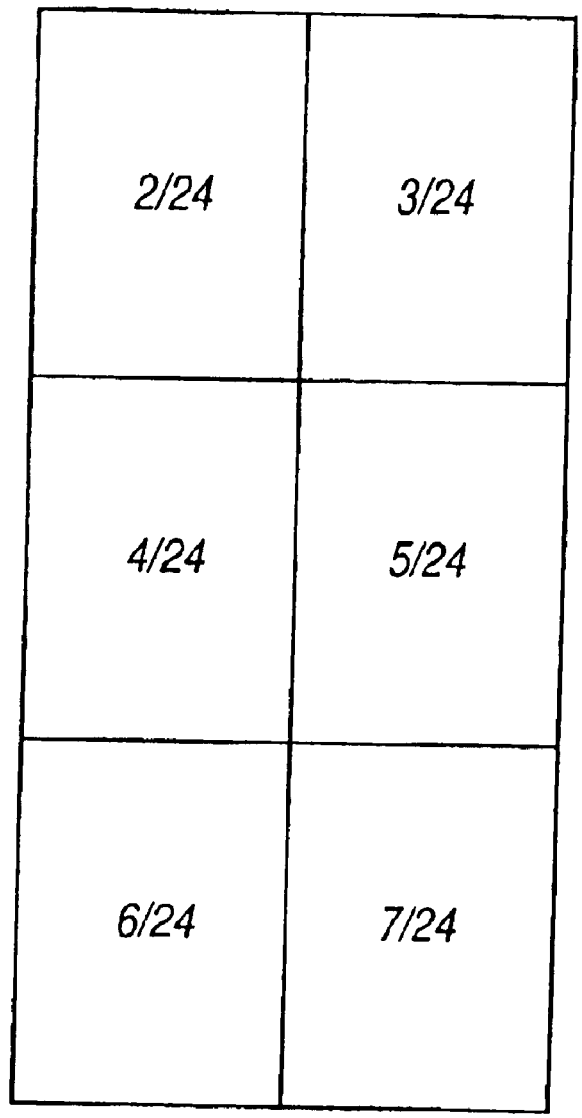
FIGS. 1A–1F show the nucleotide and predicted amino sequence of murine NR4. The untranslated region is shown in lower case and the translated region in upper case. The conventional one-letter code for amino acids is employed, potential asparagine linked glycosylation sites are underlined and the conserved cysteine residues and WSXWS (SEQ ID NO:9) motif of haempoietin receptor family members are shown in bold. The predicted signal sequence is underlined in bold while the transmembrane domain is underlined with dashes The sequence shown is a composite derived from the analysis of 8 cDNA clones derived from 3 libraries. The 5'-end of the sequence (nucleotides −60 to 351) is derived from a single cDNA clone but is also present in genomic DNA clones that have been isolated. Boxed region—typical haempoietin receptor domain, amino acids 118–340.

Using PCR, a derivative of the NR4 cDNA was generated which encoded for the IL-3 signal sequence [SEQ ID NO:5]

and an N-terminal FLAG epitope-tag [SEQ ID NO:6] preceding the mature coding region of NR4 (Thr27 to Pro424; FIG. 1). The PCR product was cloned into the mammalian expression vector pEF-BOS (17). Constructs were sequenced in their entirety prior to use. Cells were transfected and selected as previously described (16, 18).

EXAMPLE 3

Northern Blots

Northern blots were performed as previously described (16). The source of hybridisation probes was as follows: NR4—a PCR product from nucleotide 32 to 984 (FIG. 1) and GAPDH—a cDNA fragment spanning nucleotides (19).

EXAMPLE 4

Cytokines and Experiments Using Radioiodinated Cytokines

IL-2, IL-4, IL-7, IL-9, IL-13 and IL-15 were obtained commercially (R & D Systems, Minneapolis Minn.). For radioiodination, cytokines were dissolved at a concentration of 100 µg/ml in 10 mM sodium phosphate, 150 mM NaCl (PBS), 0.02% v/v Tween 20 and 0.02% w/v sodium azide at pH 7.4. An amount of 2 µg of IL-13 was radioiodinated using the iodine monochloride method (20, 21), while 2 µg of IL-4 was radiolabelled using di-iodo-Bolton-Hunter reagent (16). Binding studies and determination of the specific radioactivity and bindability of labelled cytokines were performed as previously described (2).

For cross-linking experiments, recombinant murine IL-13 was produced as a FLAG-tagged protein in *Pichia pastoris*.

For cross-linking assays, aliquots of purified soluble IL-13Rα (NR4) were incubated with $^{125}$I-IL-13 in the presence or absence of a competitor in a final volume of 20 µl for at least 30 min at 40° C. Then 5 µl of a 12 mM solution of BS$^3$ (Bis (Sulfosuccimidyl) suberate) in PBS containing 0.02% v/v Tween-20 was added and the mixtures were incubated for 30 min at 4° C. Samples were mixed with 8 µl of 4×SDS sample buffer and analysed by 13% w/v SDS-PAGE under non-reducing conditions. Gels were dried and visualised by either autoradiography or with a PhosphoImager.

EXAMPLE 5

Proliferation Assays

The proliferation of Ba/F3 and CTLL cells in response to cytokines was measured in Lux 60 microwell HL-A plates (Nunc Inc. Ill., USA). Cells were washed three times in DMEM containing 20% v/v new born calf serum and resuspended at a concentration of 2×10$^4$ cells per ml in the same medium. Aliquots of 10 µl of the cell suspension were placed in the culture wells with 5 µl of various concentrations of purified recombinant cytokines. After 2 days of incubation at 37° C. in a fully humidified incubator containing 10% v/v CO$_2$ in air, viable cells were counted using an inverted microscope.

EXAMPLE 6

Cloning and Characterisation or Murine NR4

A library was constructed λZAP II using ApoI digested genomic DNA from embryonal stem cells and screened with a pool of $^{32}$P-labelled oligonucleotides encoding the amino acid sequence Trp-Ser-Asp-Trp-Ser (SEQ ID NO: 12) found in many members of the haemopoietin receptor family. One hybridising bacteriophage clone was found to contain a sequence that appeared to encode part of a novel member of the haemopoietin receptor family. This receptor was given the operational name NR4. The sequence of the genomic clone was used to isolate cDNAs encoding NR4 from WEHI-3B cell, peritoneal macrophage, bone marrow, skin and kidney libraries. A composite of the nucleotide sequence (SEQ ID NO: 1) and predicted amino acid sequence (SEQ ID NO: 2) of theses cDNAs is shown in FIG. 1. The NR4 cDNA is predicte4d to encode for a protein of 424 amino acid residues, containing a putative signal sequence and transmembrane domain. The extracellular region of the protein contained an immunoglobulin-like domain (amino acids 27–117), in addition to a typical haemopoietin receptor domain (amino acids 118–340)which includes four conserved cysteine residues and the characteristic Trp-Ser-Asp-Trp-Ser motif (Figure; in bold as WSXWS). The cytoplasmic tail of the new receptor was 60 amino acids in length.

EXAMPLE 7

Expression Pattern of NR4 cDNA

Figure 2:
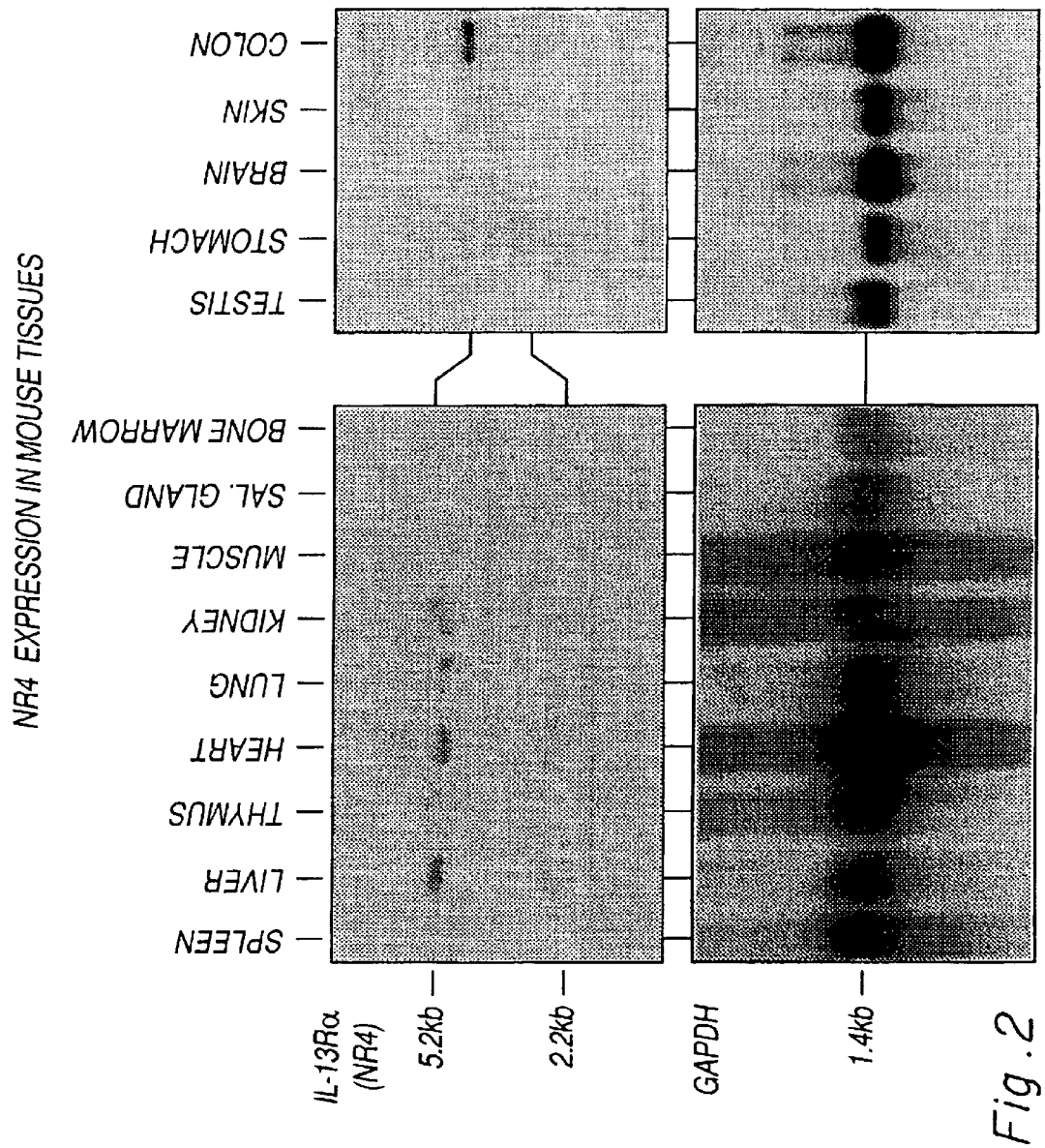
FIG. 2 is a photographic representation showing northern analysis of murine NR4 mRNA expression in selected tissues and organs.
Figure 8:
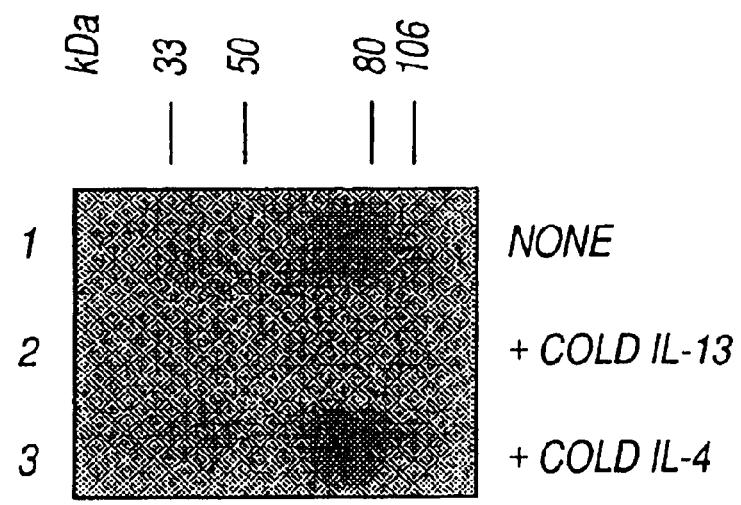
FIG. 8 is a photographic representation showing $^{125}$I-IL-13 cross-linking to soluble NR4. Lane: $^{125}$I-IL13 (100,000 cpm)+2 μg/ml soluble NR4; Lane 2: $^{125}$I-IL-13 (100,000 cpm)+2 μg/ml soluble NR4 in the presence of excess unlabelled IL-13; Lane 3: $^{125}$I-IL-1$_3$ (100,000 cpm)+2 μl g/ml soluble NR4 in the presence of excess unlabelled IL-4.

The pattern of NR4 mRNA expression was examined by Northern analyses. Two hybridising species of 5.2 and 2.2 kb in length were detected in mRNA from most tissues (FIG. 2). NR4 mRNA was not detectable in skeletal muscle (FIG. 2). FIG. 8 shows expression of NR4 in mouse tissues.

EXAMPLE 8

Figure 4A:
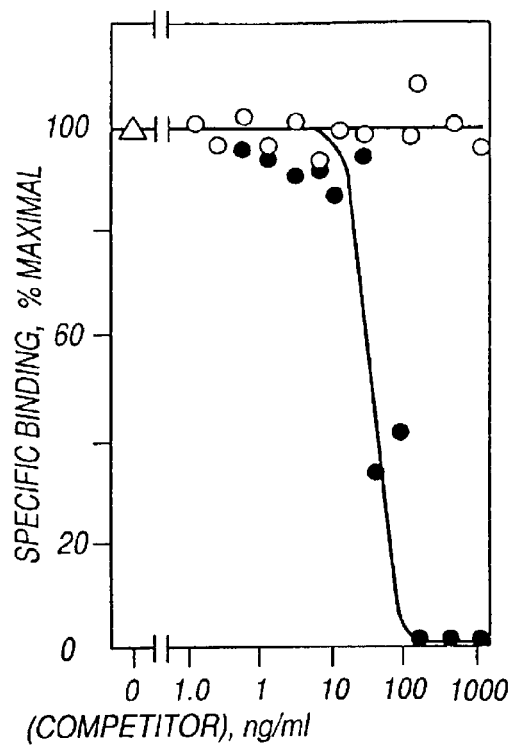
FIGS. 4A–4D show specificity of IL-4 and IL-13 binding; the ability of IL-4(°) and IL-13(•) to compete for $^{125}$I-IL13 binding to COS cells expressing the IL-13Rα(NR4) (FIG. 4A) and CTLL cells expressing the IL-13Rα (NR4) (FIG. 4C) or to compete for $^{125}$I-IL-4 binding to CTLL cells (FIG. 4) and CTLL cells expressing the IL-13Rα(NR4) (FIG. 4). Binding was carried out a 4° C. for 2 to 4 hours and the data expressed as a percentage of the specific binding observed in the absence of a competitor (Δ).

NR4 Encodes the IL-13 Receptor α-Chain (IL-13Rα)—A Specific Binding Subunit of the IL-13 Receptor The apparent molecular mass is from about 50,000 to about 70,000 daltons and more particularly about 55,000 to about 65,000 daltons for NR4 expressed in COS cells estimated from Western blots using an anti-FLAG antibody. This suggested that NR4 might encode the binding subunit of the IL-13 receptor in order to test this possibility, NR4 was expressed in COS cells. Untransfected COS cells expressed relatively low levels of IL-4 and IL-13 receptors. Upon transfection with a plasmid containing the NR4 cDNA, the number of IL-13 receptors but not IL-4 receptors expressed by COS cells was dramatically increased (FIG. 3A, 100,000 to 500,000 receptors per cell). The affinity of IL-13 for NR4 expressed by COS cells was low ($K_D$~2–10 nM) and binding was specific since it could compete with unlabelled IL-13 (FIG. 4A) but not other cytokines including IL-2, IL-4, IL-7, IL-9 or IL-15. These results suggest that NR4 is the IL-13 receptor α-chain (IL-13Rα).

EXAMPLE 9

Figure 3A:
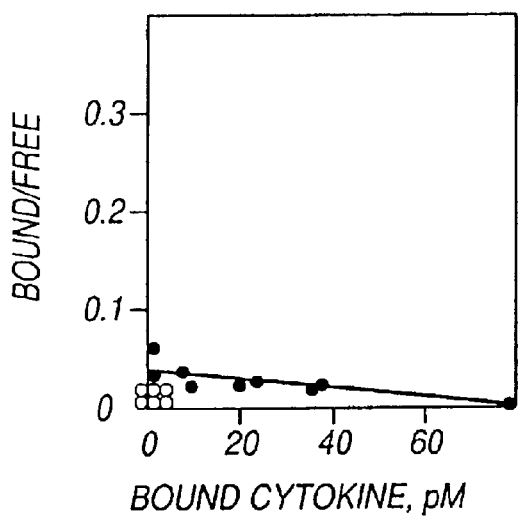
FIGS. 3A–3B depict saturation IL-4(°) and IL-13 (•) binding to COS cells expressing the IL-13Rα(NR4) (FIG. 3A), CTLL cells (FIG. 3B) and CTLL cells expressing the IL-13Rα(NR4) (FIG. 3C). Data have been normalized to $1 \times 10^4$ COS cells and $1 \times 10^6$ CTLL cells and binding was carried out on ice for 2 to 4 hours.
Figure 3B:
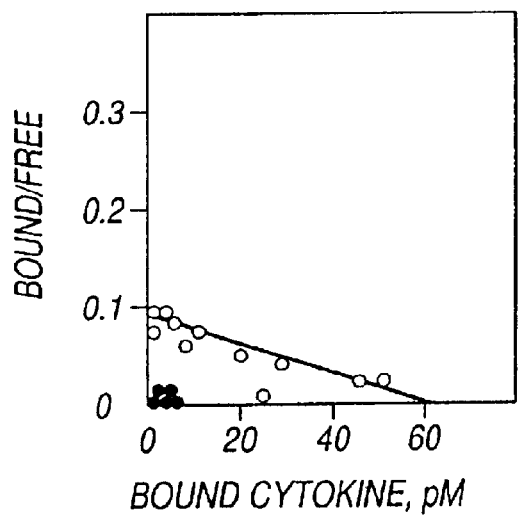
Figure 3C:
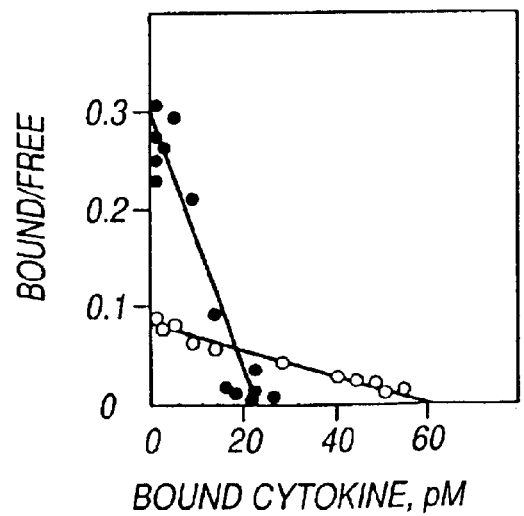
Figure 4B:
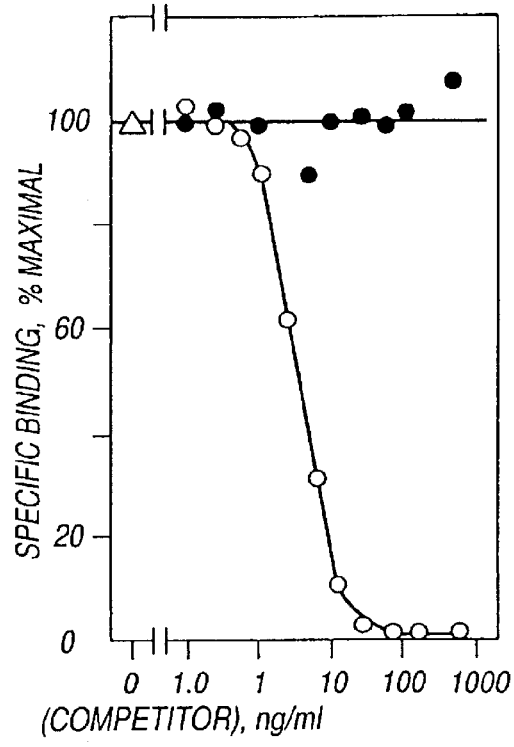
Figure 4C:
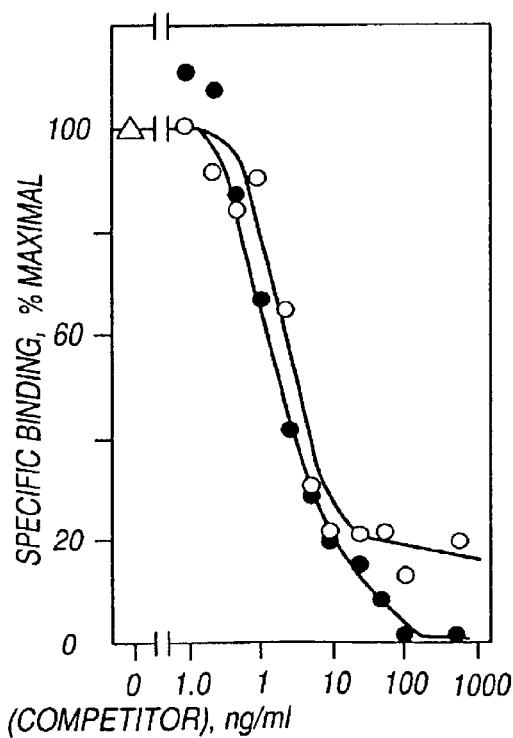
Figure 4D:
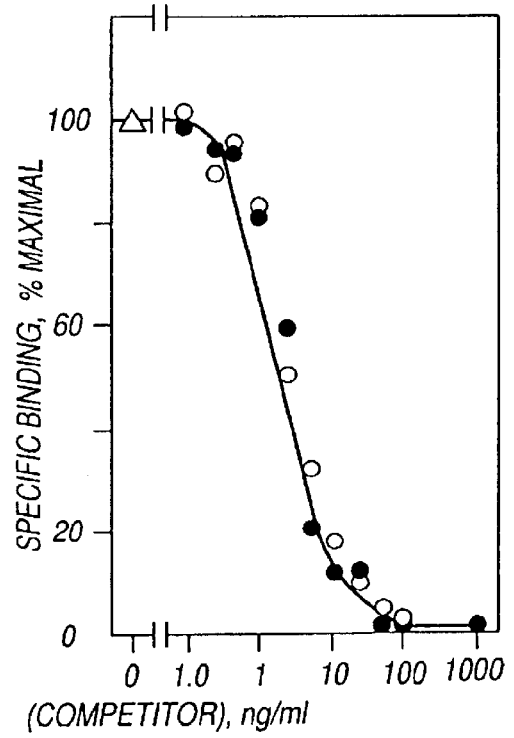

The IL-13Rα (NR4) and the IL-4Rα are Shared Components of the IL-4 and IL-13 Receptors In order to investigate the relationship between IL-4 and IL-13 receptors, the IL-4 responsive cell line CTLL was examined. Parental CTLL cells expressed a single class of IL-4 receptor ($K_D$~660 pM; ~3600 receptors per cell) but no detectable IL-13 receptors (FIG. 3B). The IL-4 receptors expressed by CTLL cells appeared to be specific since binding of $^{125}$I-IL-4 could compete with unlabelled IL-4 but not IL-13 (FIG. 4B). Upon expression of the IL-13Rα (NR4) in CTLL cells no change was observed in the number or affinity of IL-4 receptors, while a single class of high affinity IL-13 receptors was detected (FIG. 3C; $K_D$~75 pM; 1350 receptors per cell). The affinity of IL-13 for the IL-13Rα (NR4) expressed in CTLL cells was higher than in COS cells, suggesting that the former expressed a protein capable of interacting with the IL-13Rα (NR4) to increase the affinity for IL-13. A likely candidate based on previous studies is the IL-4Rα. In order to explore this possibility the ability of IL-4 to compete with $^{125}$I-IL-13 for binding to CTLL cells expressing the IL-13Rα (NR4) was assessed. FIG. 4B shows that IL-4 and IL-13 were equally effective in competing for $^{125}$I-IL-13 binding ($IC_{50}$~300 pM; FIG. 4C) and, in addition, were able to compete with $^{125}$I-IL-4 for binding ($IC_{50}$~300 pm; FIG. 4D).

EXAMPLE 10

Expression of the IL-13Rα (NR4) is necessary for transduction of a Proliferative Signal by IL-13

Figure 5A:
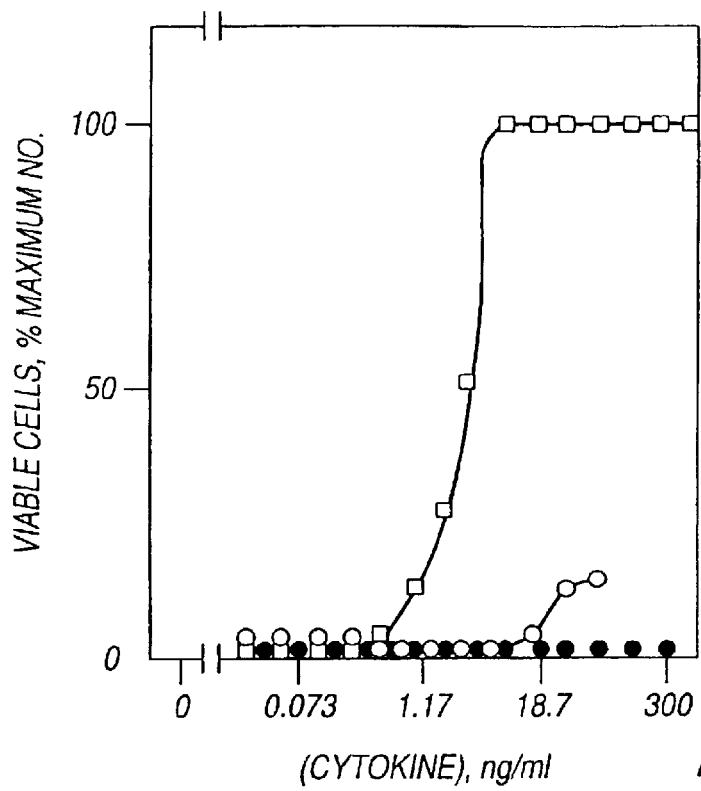
FIGS. 5A–5B show factor dependent proliferation of cells expressing NR4. Two hundred CTLL cells (FIG. 5) or CTLL cells (FIG. 5) expressing the IL-13Rα (NR4) were incubated in the absence of cytokine or with various concentrations of IL-2 (□). IL-4(°) or IL-13 (•). After 48 hours viable cells were counted and data were expressed as a percentage of the number of viable cells observed with a maximal concentration of IL-2.
Figure 5B:
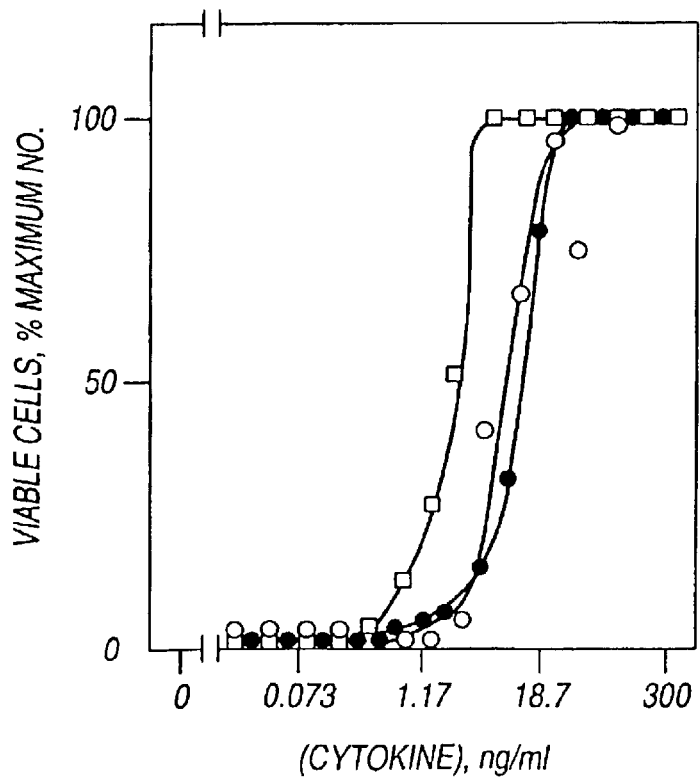

CTLL cells require the addition of exogenous cytokines for survival and proliferation. IL-2 was found to be a potent proliferative stimulus for CTLL cells ($EC_{50}$~100–200 pM), while IL-4 was relatively weak ($EC_{50}$2–7 nM) and IL-13 was inactive (FIG. 5A). Expression of the IL-13Rα (NR4) in CTLL cells resulted in the ability to survive and proliferate weakly in response to IL-13 ($EC_{50}$~700 pM) and to proliferate somewhat more strongly than parental cells in response to IL-4 ($EC_{50}$~700 pM; FIG. 5B).

EXAMPLE 11

Cloning of Human IL13Rα (NR4)

Figures 6, 10:
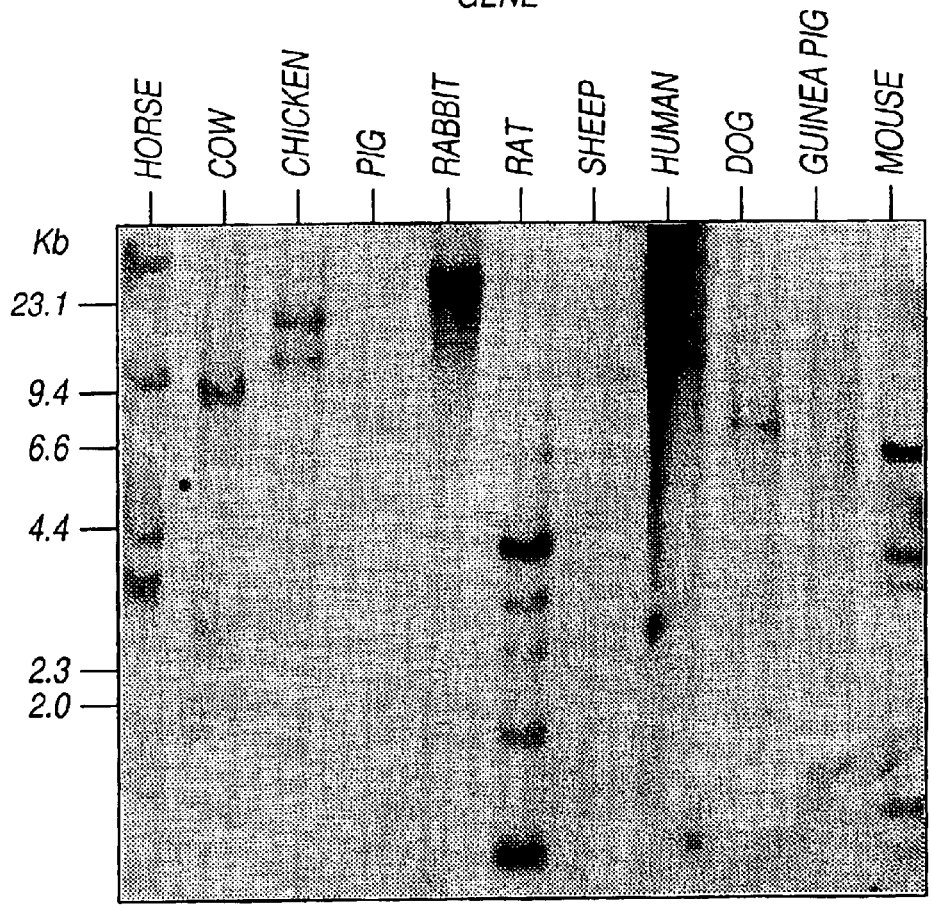
FIG. 6 is a photographic representation showing cross-species conservation of NR4 (IL-13Rα) gene.
FIG. 10 is a representation of the N-terminal amino acid sequence of murine NR4 (SEQ ID NOS: 10 and 11).

In order to determine whether genes homologous to murine IL-13Rα (NR4) exist in other vertebrate species, a probe encompassing nucleotides 840 to 1270 of murine IL-13Rα (NR4) was hybridised to EcoRI digested genomic DNA from various species. Hybridisation was carried out in 500 mM $Na_2HPO_4$ (~5×SSC) at 50° C. overnight. The filter was washed in 40 mM $Na_2HPO_4$ (~0.2×SSC) at 50° C. for 2 hours and exposed to autoradiographic film for 48 hours. FIG. 6 illustrates that relatively few (1 to 5) hybridising bands are observed in genomic DNA from various species, including human. This suggests that it is feasible to clone human IL-13Rα (NR4) using a murine cDNA probe. A human bone marrow cDNA library clones in the λZAPII bacteriophage was therefore screened with two probes (nucleotides 82–840 and 840 to 1270) from the murine IL-13Rα (NR4) cDNA. Hybridisation was carried out overnight in 6×SSC, 0.1% w/v SDS at 42° C. Filters were washed at 2×SSC, 0.1% w/v SDS at 50° C. for 2 hours and exposed for 48 hours to autoradiographic film. Plaques that hybridised to both murine IL-13Rα (NR4) probes were picked and purified in the conventional manner. The cDNA inserts form the hybridising bacteriophage were excised into the pBluescript plasmid and sequenced in their entirety using an ABI automated sequencer.

FIG. 7 shows a composite of the sequence of the clones isolated and reveals that the clones encode a protein that shares a high degree of sequence similarity with murine IL-13Rα (NR4). The clones encode the entire coding region of the protein. The high degree of sequence similarity (320/425 amino acids ~75%) predicates that this cDNA is the human homologue of the murine IL-13Rα (NR4). The nucleotide sequence is represented as SEQ ID NO:3 and the amino acid sequence is SEQ ED NO:4.

EXAMPLE 12

Soluble Murine IL-13Rα (NR4) binds IL-13

Constructs were engineered to express soluble versions of NR4 with an N-terminal "FLAG" epitope (International Biotechnologies/Eastman Kodak, New Haven Conn.). First a derivative of the mammalian expression vector pEF-BOS was generated so that it contained DNA encoding the signal sequence of murine IL-3 (MVLASSTTSIHTMLLLLLMLFHLGLQASIS [SEQ ID NO:5]) and the FLAG epitope (DYKDDDDK [SEQ ID NO:6]), followed by a unique XbaI cloning site. This vector was named pEF/IL3SIG/FLAG. The mature extracellular part of the NR4 coding region (Thr27 to Thr344) was generated by PCR using primers 1478 and 1480. The resulting product was digested with XbaI and was cloned into the XbaI site of pEF/IL3SIG/FLAG to give pEF/IL3SIG/FLAG/sol NR4. The identity of the construct was confirmed by dideoxy sequencing.

OLIGO 1478 5' AGCTTCTAGAACAGAAGTTCAGC-CACCTGTG 3' [SEQ ID NO:7];
OLIGO 1480 5' AACTCCACCTTCTACACCACCT-GATCTAGA 3' [SEQ ID NO:8].

After transfection into CHO cells, expressed, soluble NR4 was purified from CHO cell-conditioned medium on an anti-FLAG antibody (M2) affinity column by elution with free FLAG peptide (Science Imaging Systems).

Consistent with the low affinity of IL-13 for NR4 expressed by COS cells, purified soluble NR4 appeared unable to bind IL-13 as assessed by gel filtration chromatography. However, using sensitive cross-linking assays, the ability of soluble IL-13Rα (NR4) in bind IL-13 was demonstrated (FIG. 8, lane 1). This interaction was competed for by unlabelled IL-13 but not by unlabelled IL-4 (FIG. 8, lanes 2 and 3).

EXAMPLE 13

Polyclonal Antisera to Soluble IL-13Rα (NR4)

Figure 9:
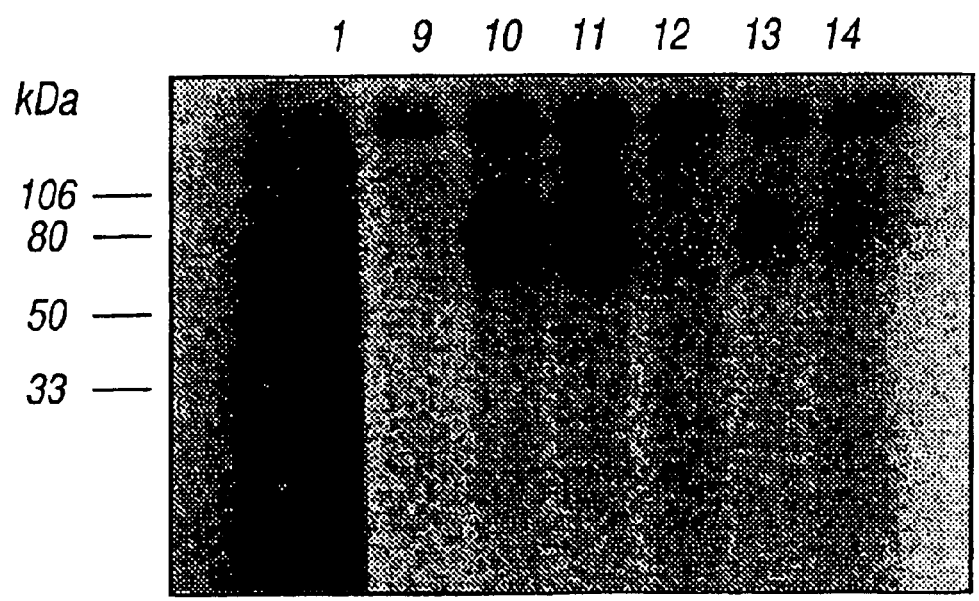
FIG. 9 is a photographic representation of immunoprecipitation by anti-NR4 polyclonal antisera of cross-linked $^{125}$I-IL13 with IL-13Rα (NR4). Lanes 9–11: soluble IL-13Rα(30 μl of 3 μg/ml) cross-linked to $^{125}$I-IL-13 (750,000 cpm) and immunoprecipitated with control rabbit serum, or with anti-NR4 polyclonal antiserum in the presence or absence of 100 μg/ml FLAG peptide, respectively; Lanes 12–14: soluble IL-13Rα (NR4) (30 μl of 3 μg/ml) cross-linked to $^{125}$I-IL13 (750,000 cpm) in the presence of 0.5 μg/ml unlabelled IL-13 and immunoprecipitated with an anti-IL-13Rα (NR4) polyclonal antiserum also in the presence or absence of 100 μg/ml FLAG peptide, respectively.

A polyclonal antiserum to NR4 was prepared by injecting purified soluble NR4 into rabbits which were bled after 3 months. This antisera immunoprecipitated the cross-linked product of $^{125}$I-IL-13 with soluble NR4 (FIG. 9, lane 11) while no immunoprecipitation was observed with pre-immune serum (FIG. 9, lane 9). Immunoprecipitation of the complex was not inhibited by the FLAG peptide (FIG. 9, lane 10).

The immunoprecipitation assay was conducted as follows:

The cross-linking reactions were terminated by the addition of Tris-HCl, pH 7.5, to a final concentration of 40 mM. The samples wee then mixed with 1:50 diluted control rabbit serum or anti-NR4 serum which had been pre-incubated with or without FLAG peptide. After incubation for 30 min at 4° C., the mixtures were added to 40 μl of 50% v/v protein G-Sepharose gel slurry (Pharmacia) and incubated for 30 min at 4° C. The samples were centrifuged and the protein G beads were washed 3×0.5 ml PBS, mixed with 40 μl of 2× concentrated SDS-PAGE sample buffer and heated for 2 min at 95° C. The supernatants were analysed by 13% w/v SDS-PAGE under non-reducing conditions.

EXAMPLE 14

N-terminal Amino Add Sequence of NR4

The N-terminal amino acid sequence of NR4 was determined and is shown in FIG. 10.

EXAMPLE 15

Assay for IL-13

IL-13 is a cytokine that is implicated in the production of IgE, the immunoglobulin isotype important in allergic diseases such as asthma. Monitoring IL-13 levels may, therefore, be an important diagnostic. Since IL-4 and IL-13 share many biological effects, generating an assay that discriminates these cytokines is also important.

NR4 expressed in COS cells binds $^{125}$I-IL-13. This binding is inhibited in a dose dependent manner by unlabelled IL-13, in the presence of a large amount of irrelevant protein such as calf serum or human serum. IL-4 shows no ability to compete for $^{125}$I-IL-13 binding in this situation and, therefore, this assay appears to be specific for IL-13.

The assay is set up by coating soluble NR4 on ELISA plates and using, for example, fluorescent labelled IL-13 as die probe. The presence of unlabelled IL-13 in a test sample then registers as a decrease in the fluorescent signal.

Similar assays are set up that measure both IL-4 and IL-13 by using cells that express NR4 and IL-4 receptor α-chain. These include CTLL cells which normally express IL-4 receptor α-chain and which are engineered to express NR4. Binding of $^{125}$I-IL-13 or $^{125}$I-IL-4 can be inhibited by unlabelled forms of both IL-4 and IL-13.

EXAMPLE 16

Modifications to IL-4 and IL-13

Mutations are introduced into regions of the molecules that are predicated to be functionally important. In the case of NR4, this includes the region that interacts with IL-13, the region which interacts with IL-4 receptor α-chain or the region that interacts with IL-4 when this cytokine is bound to die IL-4 receptor α-chain. These regions are determined by direct experiment, for example, by solving the structure of NR4 or complexes of NR4 with other proteins like IL-4, IL-13 and the IL-4 receptor α-chain or by modeling these proteins on similar proteins for which structural information exists, for example, the growth hormone/growth hormone receptor complex. Resulting NR4 mutants are then individually tested for improved function.

In an alternative method, random mutations are generated in the molecules. Suitable techniques include synthesis of NR4 cDNA using a polymerase and reaction conditions that promote incorporation of the incorrect dNTP and use of a technique called DNA shuffling (23, 24, 25, 26).

After generating random mutants of the cDNA of interest, potentially useful mutants are selected. In die case of NR4, an assay is based on knowledge that if NR4 is expressed in cells which lack IL-4 receptor α-chain (e.g. COS cells), then cells are obtained that cannot bind IL-4 with any detectable affinity and binds IL-13 with low affinity. Thus, if COS cells are transfected with Nr4 and allowed to bind FITC-conjugated IL-4 and phycoerythrin-conjugated IL-13, the unbound ligand washed away, the no IL-4 will bind and any IL-13 that had bound would dissociate during die washing.

If these cells are FACS-sorted, then little or no signal in either the FITC or PE channel would be obtained. COS cells are transfected with $10^6$ to $10^7$ random mutants of NR4 and processed for binding. Any cells sorted which bind the cytokines better than those transfected with wild type NR4 can be FACS sorted. The plasmids containing these "improved" NR4 cDNAs may be recovered, expanded in *E. coli* and used again in COS cells to confirm the improvement. Any mutants that are consistently better can then be used for the introduction of further random changes into an order to get even better molecules. This iterative process may be repeated several times.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

Bibliography

1. Du, X. X. and Williams, D. A. (1994) *Blood* 83: 2023–2030.
2. Yang, Y. C. and Yin, T. (1992) *Biofactors* 4: 15–21.
3. Paul, S. R., Bennett, F. Calvetti, J. A., Kelleher, K., Wood, C. R., O'Hara, R. J. J., Leary, A. C., Sibley, B., Clark, S. C., Williams, D. A. and Yang, Y.-C. (1990) *Proc. Natl. Acad. Sci. USA* 87: 7512.
4. Musashi, M., Clark. S. C., Sudo, T., Urdal, D. L., and Ogawa, M. (1991) *Blood* 78: 1448–1451.
5. Schibler, K. R., Yang, Y. C. and Christensen, R. D. (1992) *Blood* 80: 900–3.
6. Tsuji, K., Lyman, S. D., Sudo, T., Clark, S. C., and Ogawa, M. (1992) *Blood* 79: 2855–60.
7. Burstein, S. A., Mei, R. L., Henthorn, I., Friese, P. and turner, K. (1992) *J. Cell. Physiol.* 153. 305–12.
8. Hangoc, G., Yin, T., Cooper, S., Schendel, P., Yang, Y. C. and Broxmeyer, H. E. (1993) *Blood* 81: 965–72.
9. Teramura, M., Kobayashi, S., Hoshino, S., Oshimi, K. and Mizoguchi, H. (1992) *Blood* 79: 327–31.
10. Yonemura, Y., Kawakita, M., Masuda, T., Fujimoto, K., Kato, K. and Takatsuki, K. (1992) *Exp. Hematol.* 20: 1011–6.
11. Baumann, H. and Schendel, P. (1991) *J. Biol. Chem.* 266: 20424–7.
12. Kawashima, I., Ohsumi, J., Mita-Honjo, K., Shimoda-Takano, K., Ishikawa, H., Sakakibara, S., Miyadai, K. and Takiguchi, Y. (1991) *Febs. Lett.* 283: 199–202.
13. Keller, D. C., Du, X. X., Srour, E. f., Hoffman, R. and Williams, D. A. (1993) *Blood* 82: 1428–35.
14. McKenzie, A. N. J. and Zurawski, G. (1994) *Guidebood to cytokines and their receptors*, Oxford University Press. Oxford.
15. Zurawski, G. and de Vries, J. E. (1994) *Immunol. Today* 15: 19–26.
16. Hilton, D. J., Hilton, A. A., Raicevic, A., Rakar, S., Harrison-Smith, M., Gough, N. M., Begley, C. G., Metcalf, D., Nicola, N. A. and Wilson, T. A. (1994) *EMBO J.* 13: 4765–4775.
17. Mizushima, S. and Nagata, S. (1990) *Nucleic Acids Res.* 18: 5322.
18. Lock, P., Metcalf, D. and Nicola, N. A. (1994) *Proc. Natl. Acad. Sci. USA* 91: 252–256.
19. Dugaiczyk, A. et al (1983) *Biochiemistry* 22: 1605–1613.
20. Contreras, M. A., Bale, W. F. and Spar, I. L. (1983) *Methods in Enzymol.* 92: 277–292.
21. Hilton, D. J. and Nicola, N. A. (1992) *J. Biol. Chem.* 267: 10238–10247.
22. Sambrook, J., Fritsch, E. F. and Maniatis, T. (1989) *Molecular cloninig: A Laboratory Manual* Cold Spring Harbor Laboratory, Cold Spring Harbor, N.Y.
23. Stemmer, W. P. C., (1994) *Nature* 370: 389–391.
24. Stemmer, W. P. C., (1995) *Biotechnology* 13: 549–553.
25. Gassmann et at (1995) *Proc. Natl. Acad. Sci. USA* 92: 1292–1296.
26. Grameri et al (1996) *Nature Biotechnology* 14: 315–319.

What is claimed is:

1. An isolated antibody generated using an IL-13 receptor α-chain polypeptide comprising all or part of SEQ ID NO: 4, which antibody binds to an IL-13 receptor α-chain.

2. An isolated antibody which binds specifically to an IL-13 receptor α-chain consisting of the sequence of SEQ ID NO: 4.

3. The isolated antibody according to claim 1 or 2, wherein said antibody inhibits the interaction between IL-13 and an IL-13 receptor α-chain.

4. The isolated antibody according to claim 1 or 2, wherein said antibody inhibits the interaction between IL-13 and an IL-13 receptor α-chain consisting of the sequence of SEQ ID NO: 4.

5. The isolated antibody according to claim 1 or 2, wherein said antibody inhibits the interaction between an IL-13 receptor α-chain and an IL-4 receptor α-chain.

6. The isolated antibody according to claim 1 or 2, wherein said antibody is a polyclonal antibody.

7. The isolated antibody according to claim 1 or 2, wherein said antibody is a monoclonal antibody.

8. A composition comprising the antibody according to claim 1 or 2 and at least one of a pharmaceutically acceptable carrier or a diluent.

9. A composition comprising the antibody according to claim 3 and at least one of a pharmaceutically acceptable carrier or a diluent.

10. A composition comprising the antibody according to claim 4 and at least one of a pharmaceutically accepatable carrier or a diluent.

11. A composition comprising the antibody according to claim 5 and at least one of a pharmaceutically accepatable carrier or a diluent.

12. A composition comprising the antibody according to claim 6 and at least one of a pharmaceutically acceptable carrier or a diluent.

13. A composition comprising the antibody according to claim 7 and at least one of a pharmaceutically accepatable carrier or a diluent.

14. An isolated antibody against an IL-13 receptor α-chain or an antigen-binding fragment thereof, wherein said antibody or said antigen-binding fragment binds SEQ ID NO: 4.

15. The isolated antibody or antigen-binding fragment of claim 14, wherein said IL-13 receptor α-chain consists of SEQ ID NO: 4.

\* \* \* \* \*